(12) United States Patent
Dahlquist

(10) Patent No.: US 9,855,350 B1
(45) Date of Patent: Jan. 2, 2018

(54) FLUID DISPERSAL SYSTEM WITH INTEGRATED FUNCTIONAL LIGHTING

(71) Applicant: Kevin James Dahlquist, Charlotte, NC (US)

(72) Inventor: Kevin James Dahlquist, Charlotte, NC (US)

( * ) Notice: Subject to any disclaimer, the term of this patent is extended or adjusted under 35 U.S.C. 154(b) by 255 days.

(21) Appl. No.: 14/454,700

(22) Filed: Aug. 7, 2014

Related U.S. Application Data

(63) Continuation-in-part of application No. 14/184,948, filed on Feb. 20, 2014, now abandoned.

(60) Provisional application No. 61/766,921, filed on Feb. 20, 2013, provisional application No. 61/799,228, filed on Mar. 15, 2013.

(51) Int. Cl.
*A61L 2/10* (2006.01)
*B05B 11/00* (2006.01)

(52) U.S. Cl.
CPC .............. *A61L 2/10* (2013.01); *B05B 11/3011* (2013.01)

(58) Field of Classification Search
CPC ................................ A61L 2/10; B05B 11/3011
USPC .......... 239/289, 71, 588, 525, 288, 112, 526
See application file for complete search history.

(56) References Cited

U.S. PATENT DOCUMENTS

| | | | |
|---|---|---|---|
| 2,754,225 A * | 7/1956 | Gfeller .................... | B05B 5/032 118/726 |
| 5,301,756 A * | 4/1994 | Relyea ................... | A62C 27/00 169/24 |
| 5,378,493 A * | 1/1995 | Zivkovic ............... | F27D 1/1647 118/713 |
| 5,486,154 A * | 1/1996 | Kelleher ............ | A61B 1/00105 600/104 |
| 5,943,075 A * | 8/1999 | Lee ........................ | B01L 3/0268 239/102.2 |
| 6,229,563 B1 * | 5/2001 | Miller, II ................ | F27D 21/02 348/82 |
| 6,409,657 B1 * | 6/2002 | Kawano ............. | A61B 1/00091 600/127 |
| 6,439,472 B1 * | 8/2002 | Lin ........................ | B05B 15/00 239/16 |
| 6,857,582 B1 * | 2/2005 | Wang ................... | B60Q 1/0017 239/17 |
| 6,885,114 B2 * | 4/2005 | Baarman ................ | C02F 1/325 239/265.11 |
| 6,896,192 B2 * | 5/2005 | Horan ................... | B05B 12/004 239/1 |
| 6,983,899 B2 * | 1/2006 | Melendez .............. | B05B 1/202 118/315 |
| 7,787,232 B2 * | 8/2010 | Abatemarco ........... | A45B 3/04 361/232 |

(Continued)

*Primary Examiner* — Arthur O Hall
*Assistant Examiner* — Steven M Cernoch
(74) *Attorney, Agent, or Firm* — Tillman Wright, PLLC; James D. Wright; David R. Higgins

(57) ABSTRACT

A fluid dispersal system with integrated UV lighting includes a reservoir of fluid, a sprayer head connected to the fluid reservoir, a nozzle, and an ultraviolet lighting element. The nozzle is supported by the sprayer head and is in fluid communication with the reservoir to disperse fluid from the reservoir in a spray direction. The ultraviolet lighting element is supported by the sprayer head adjacent the spray nozzle, and directs ultraviolet light in a direction generally parallel to the spray direction. The nozzle and the lighting element may be actuated such that ultraviolet light is directed onto a surface while fluid is simultaneously dispersed onto the surface.

13 Claims, 26 Drawing Sheets

(56) References Cited

U.S. PATENT DOCUMENTS

| | | | |
|---|---|---|---|
| 8,210,395 B1 | 7/2012 | Morris | |
| 8,322,634 B2* | 12/2012 | Cunningham | A61H 7/003 239/398 |
| 8,363,376 B2* | 1/2013 | Abatemarco | A45B 3/04 361/232 |
| 2002/0139865 A1* | 10/2002 | Mulvaney | A61L 2/08 239/20 |
| 2003/0178503 A1* | 9/2003 | Horan | B05B 12/004 239/73 |
| 2006/0283981 A1* | 12/2006 | Mead | B05B 15/066 239/526 |
| 2007/0189834 A1 | 8/2007 | McKay, Sr. | |
| 2010/0176221 A1* | 7/2010 | Cunningham | A61H 7/003 239/525 |
| 2010/0304874 A1* | 12/2010 | Abatemarco | A45B 3/04 463/47.3 |
| 2011/0240757 A1* | 10/2011 | Selk | B05B 17/08 239/18 |
| 2013/0330285 A1* | 12/2013 | Smart | A61M 35/00 424/59 |
| 2014/0246512 A1* | 9/2014 | DeGeorge | A47L 11/00 239/71 |

\* cited by examiner

FLUID DISPERSAL SYSTEM WITH INTEGRATED FUNCTIONAL LIGHTING

CROSS-REFERENCE TO RELATED APPLICATIONS

The present application is a U.S. continuation-in-part patent application of, and claims priority under 35 U.S.C. §120 to, U.S. nonprovisional patent application Ser. No. 14/184,948, filed Feb. 20, 2014, which patent application is a U.S. non-provisional patent application of, and claims priority under 35 U.S.C. §119(e) to, each of the following U.S. provisional patent applications, each of which is expressly incorporated herein by reference in its entirety:
  (a) U.S. provisional patent application Ser. No. 61/766,921, filed Feb. 20, 2013 and entitled "SPRAY CONTAINER WITH INTEGRATED FUNCTIONAL LIGHTING;" and
  (b) U.S. provisional patent application Ser. No. 61/799,228, filed Mar. 15, 2013 and entitled, "SPRAY CONTAINER WITH INSECT ATTRACTING FEATURES," a copy of which is attached hereto as Appendix A, which is likewise expressly incorporated herein by reference in its entirety.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE PRESENT INVENTION

Field of the Present Invention

The present invention relates generally to fluid spray bottles, and, in particular, to lighting features integrated with spray nozzles.

Background

Spray bottles are well known. Common types include variable spray nozzles, trigger activated pump designs, and aerosol propellant canisters. Different variations exist to improve comfort, ease of use, and a variety of spray patterns.

LED lighting is a well-known technology. Different wave lengths of visible light can be used to illuminate chemical substances including those of dangerous or undesirable composition. In additional to common color shades which can be used to change observed contrast, the ultraviolet spectrum of light can particularly be utilized to illuminate contaminants and chemicals invisible to the naked eye. UV lighting is also known to be damaging to harmful bacteria, fungus, and mold under certain conditions. As such, UV lighting can be used not only to illuminate areas of concern, but also to actively sanitize the same areas utilizing exposure to the light.

Alternative designs have integrated motorized pumping technologies, as well as ionizing and ozonating technologies to improve cleaning effectiveness.

UV lighting has been used separately to illuminate harmful elements of a surface or room. UV lighting has been used in the process of neutralizing harmful properties of these elements as well.

Some spray bottles making use of lighting elements are known. U.S. Pat. No. 8,210,395 to Morris discloses a spray dispenser (such as a bottle of perfume) that utilizes small visible light emitters (which may be LEDs) adjacent a nozzle to help a user find the location or direction of the nozzle, but the light has to be visible so as to carry out its function, and further, the light is intended to be on only when the user is searching for the location of the nozzle, and not when actually spraying the fluid. U.S. Patent Publication No. US 2007/0189834 A1 to McKay, SR, discloses a detachable black light unit stored in the body of a sprayer, but is used separately from the spray head itself and thus does not provide the convenience of mechanically linking the direction of the black light emanating from the black light unit with the direction of spray.

Thus the continued need exists for improvement in the area of cleaning and sanitizing products, particularly in the area of integrated solutions and development of a symbiotic system

SUMMARY OF THE PRESENT INVENTION

Broadly defined, the present invention according to one aspect is a fluid dispersal system with integrated UV lighting, including: a reservoir of fluid; a sprayer head connected to the fluid reservoir; a nozzle, supported by the sprayer head and in fluid communication with the reservoir, to disperse fluid from the reservoir in a spray direction; and an ultraviolet lighting element, supported by the sprayer head adjacent the spray nozzle, that directs ultraviolet light in a direction generally parallel to the spray direction.

In a feature of this aspect, the ultraviolet lighting element directs ultraviolet light while fluid is dispersed from the reservoir.

In another feature of this aspect, the nozzle is an adjustable indexed nozzle.

In another feature of this aspect, the fluid dispersal system further includes a pump system that pressurizes the fluid reservoir and a valve to release fluid through the nozzle. In a further feature, the pump system includes a pump body, a piston inserted into the pump body, and a handle on the piston, wherein the handle is actuated by a user to pressurize the fluid reservoir; and/or the pump system includes a trigger operated piston pump wherein a manually-operated trigger raises an internal piston to draw fluid up a dip tube and force it out through the nozzle.

In another feature of this aspect, the fluid dispersal system further includes an electrical switch to activate the ultraviolet lighting element. In further features, the electrical switch is manually actuated by a user, separately from actuation of the fluid dispersal; the electrical switch and fluid dispersal are actuated separately but simultaneously; and/or actuation of the electrical switch is linked mechanically to actuation of the fluid dispersal.

In another feature of this aspect, the reservoir of fluid is a pressurized reservoir.

In another feature of this aspect, the sprayer head includes a housing, the housing including a light fairing protecting the ultraviolet lighting element.

In another feature of this aspect, the ultraviolet lighting element directs ultraviolet light on a surface to be sprayed by the fluid via the spray nozzle. In a further feature, the ultraviolet lighting element directs ultraviolet light on a surface having material containing a chemical not visible to the naked human eye.

In another feature of this aspect, the fluid dispersal system further includes a rechargeable battery that powers the ultraviolet lighting element. In a further feature, the fluid dispersal system further includes a USB cable connection, integrated with the sprayer head, for recharging the rechargeable battery.

Broadly defined, the present invention according to another aspect is a fluid dispersal system with integrated lighting, including: a reservoir of fluid; a sprayer head connected to the fluid reservoir; a nozzle, supported by the sprayer head and in fluid communication with the reservoir, to disperse fluid from the reservoir in a spray direction; and a lighting element, supported by the sprayer head adjacent the spray nozzle, that directs ultraviolet light in a direction generally parallel to the spray direction; wherein the nozzle and the lighting element may be actuated such that light is directed onto a surface while fluid is simultaneously dispersed onto the surface.

In a feature of this aspect, the lighting element is an ultraviolet lighting element.

In another feature of this aspect, the fluid dispersal system further includes a first actuator for activating the lighting element and a second actuator for causing fluid dispersal.

In another feature of this aspect, the fluid dispersal system further includes an actuator for both activating the lighting element and causing fluid dispersal.

Broadly defined, the present invention according to another aspect is a modular sprayer head, for connection to a reservoir of fluid, with integrated UV lighting, including: a reservoir interface that removably connects the modular sprayer head to a reservoir of fluid; a nozzle, supported by the sprayer head and in fluid communication with the reservoir, to disperse fluid from the reservoir in a spray direction; and a lighting element, supported by the sprayer head adjacent the spray nozzle, that directs ultraviolet light in a direction generally parallel to the spray direction; wherein the nozzle and the lighting element may be actuated such that ultraviolet light is directed onto a surface while fluid is simultaneously dispersed onto the surface.

In a feature of this aspect, the modular sprayer head further includes a first actuator for activating the lighting element and a second actuator for causing fluid dispersal.

In another feature of this aspect, the modular sprayer head further includes an actuator for both activating the lighting element and causing fluid dispersal.

Broadly defined, the present invention according to another aspect is a spray container including: a reservoir of fluid; a housing; a passageway and pump arranged to pressurize the fluid reservoir; an adjustable indexed nozzle to disperse and distribute the fluid; a valve to release fluid through the nozzle; and a light or lights oriented to direct light in a direction generally parallel to the nozzle.

Broadly defined, the present invention according to another aspect is a common pump actuated fluid sprayer including, a fluid reservoir, a trigger component which acts on the pump, a sealing cap, a power source, an electrical switch and one or more lighting elements surrounding the spray nozzle and projecting light generally parallel to the spray direction, either in tandem with the trigger or operated independently.

Broadly defined, the present invention according to another aspect is a pressurized canister containing a fluid, a trigger operated valve component, a power source, an electrical switch, and one or more lighting elements surrounding the spray nozzle and projecting light generally parallel to the spray direction, either in tandem with the trigger component or operated independently.

Broadly defined, the present invention according to another aspect is a common pump actuated fluid sprayer including, a fluid reservoir, a trigger component which acts on the pump, a sealing cap, a power source, an electrical switch and one or more lighting elements, in concert with a light transmitting optic near the spray nozzle and projecting light generally parallel to the spray direction, either in tandem with the trigger or operated independently.

Broadly defined, the present invention according to another aspect is a spray container including: a reservoir of fluid; a housing; a passageway and pump arranged to deliver the fluid from the reservoir to the nozzle; a nozzle to disperse and distribute the fluid; and a light oriented to direct light in a direction generally parallel to the nozzle.

In a feature of this aspect, the light is disposed in the nozzle.

Broadly defined, the present invention according to another aspect is a spray container, including: a pressurized reservoir of fluid; a housing; a passageway through a valve from reservoir arranged to deliver fluid to nozzle; a nozzle to disperse and distribute fluid; and a light or lights disposed in a direction generally parallel to the nozzle.

Broadly defined, the present invention according to another aspect is a spray container, as shown and described.

Broadly defined, the present invention according to another aspect is a head for a spray container, including: a housing; a nozzle, at least partially supported by the housing, to disperse and distribute fluid from a reservoir; and a light, at least partially supported by the housing, to direct light in a direction generally parallel to a direction of dispersal and distribution by the nozzle.

Broadly defined, the present invention according to another aspect is a head for a spray container, as shown and described.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

Further features, embodiments, and advantages of the present invention will become apparent from the following detailed description with reference to the drawings, wherein:

FIG. 4a is a side cross-sectional view of the fluid dispersal system of FIG. 1 showing the air pressurized pump system thereof;

FIG. 4b is an exploded isometric view of the pump system of FIG. 4a;

DETAILED DESCRIPTION

Figure 1:
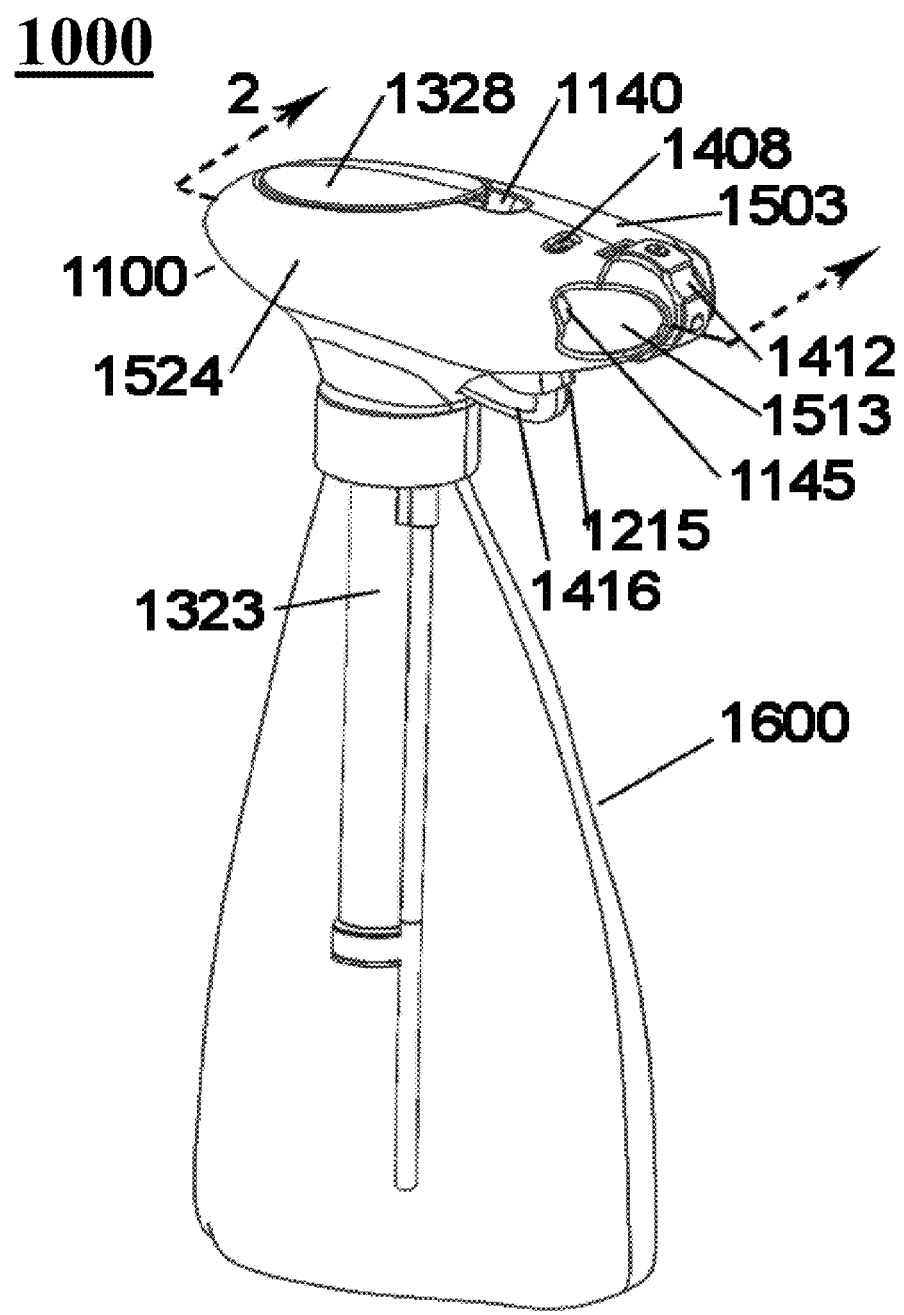
FIG. 1 is an isometric view of a lighted pressure actuated fluid dispersal system in accordance with a first preferred embodiment of the present invention.

As a preliminary matter, it will readily be understood by one having ordinary skill in the relevant art ("Ordinary Artisan") that the present invention has broad utility and application. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. §112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers," "a picnic basket having crackers without cheese," and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, in which like numerals represent like components throughout the several views, one or more preferred embodiments of the present invention are next described. The following description of one or more preferred embodiments is merely exemplary in nature and is in no way intended to limit the invention, its implementations, or uses.

Figure 2:
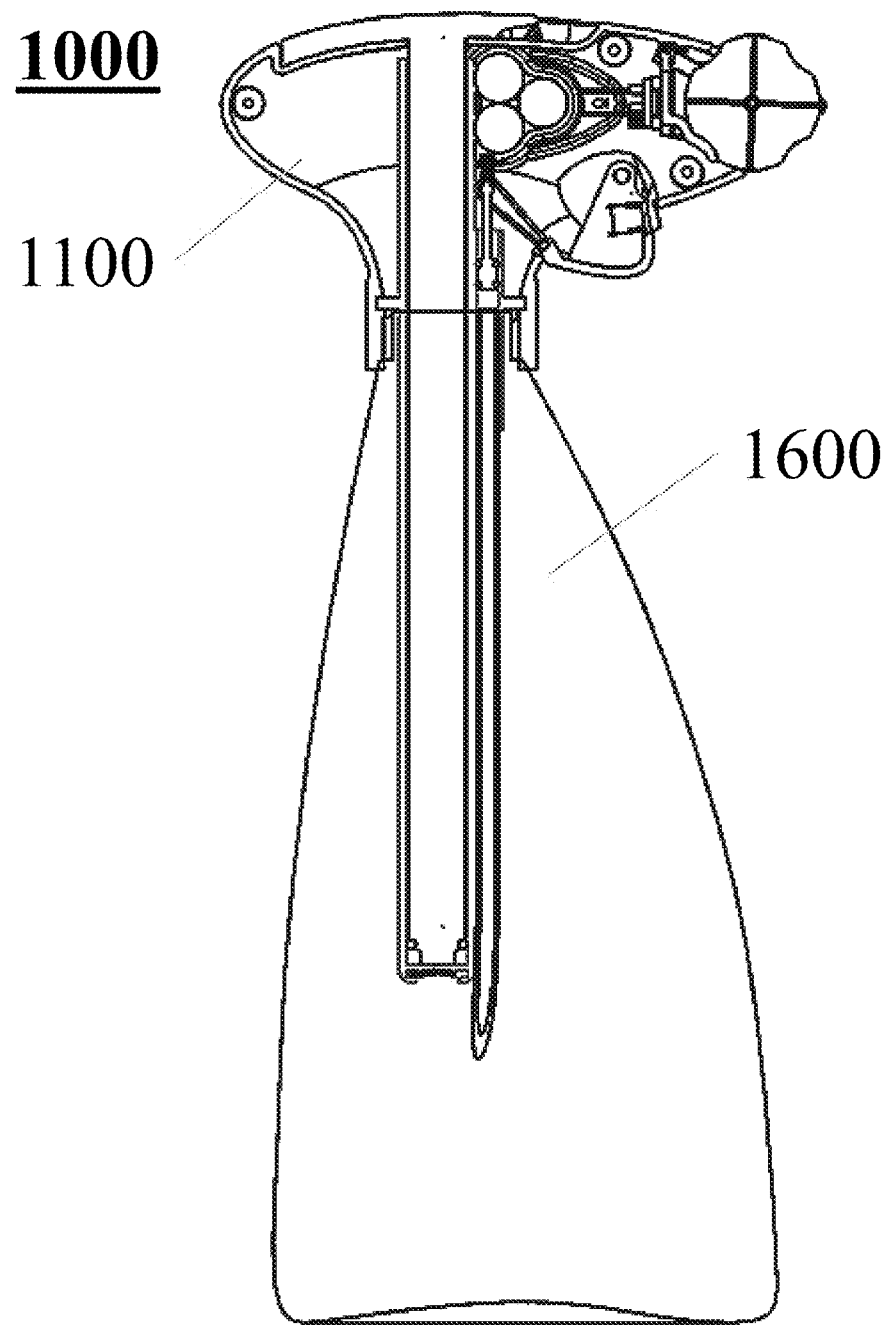
FIG. 2 is a side cross-sectional view of the fluid dispersal system of FIG. 1.

FIG. 1 is a perspective view of a lighted pressure actuated fluid dispersal system 1000 in accordance with a first preferred embodiment of the present invention; and FIG. 2 is a side cross-sectional view of the fluid dispersal system 1000 of FIG. 1, taken along line 2. As shown therein and in other illustrations, the system 1000 includes a sprayer head 1100 and a reservoir 1600, as well as various other elements, including an electrical system 1200, described below in FIG. 3; an air pressurizing pump system 1300, described below in FIG. 4a and FIG. 4b; a fluid distribution system 1400, described below in FIG. 5, and enclosure components 1500, described below in FIG. 6.

Referring to FIG. 1, the sprayer head 1100 includes a light fairing 1513, a left housing 1503, right housing 1524 and the housing contains LED light holes 1145, and a finger hole 1140. The sprayer also includes a pump body 1323, a pump handle 1328, an indicator 1408, a turret head 1412, a fluid valve switch 1416, a selectable nozzle 1412, and an electrical switch cover 1215, all of which connect to internal systems whose parts are illustrated and described in detail below.

Figure 3:
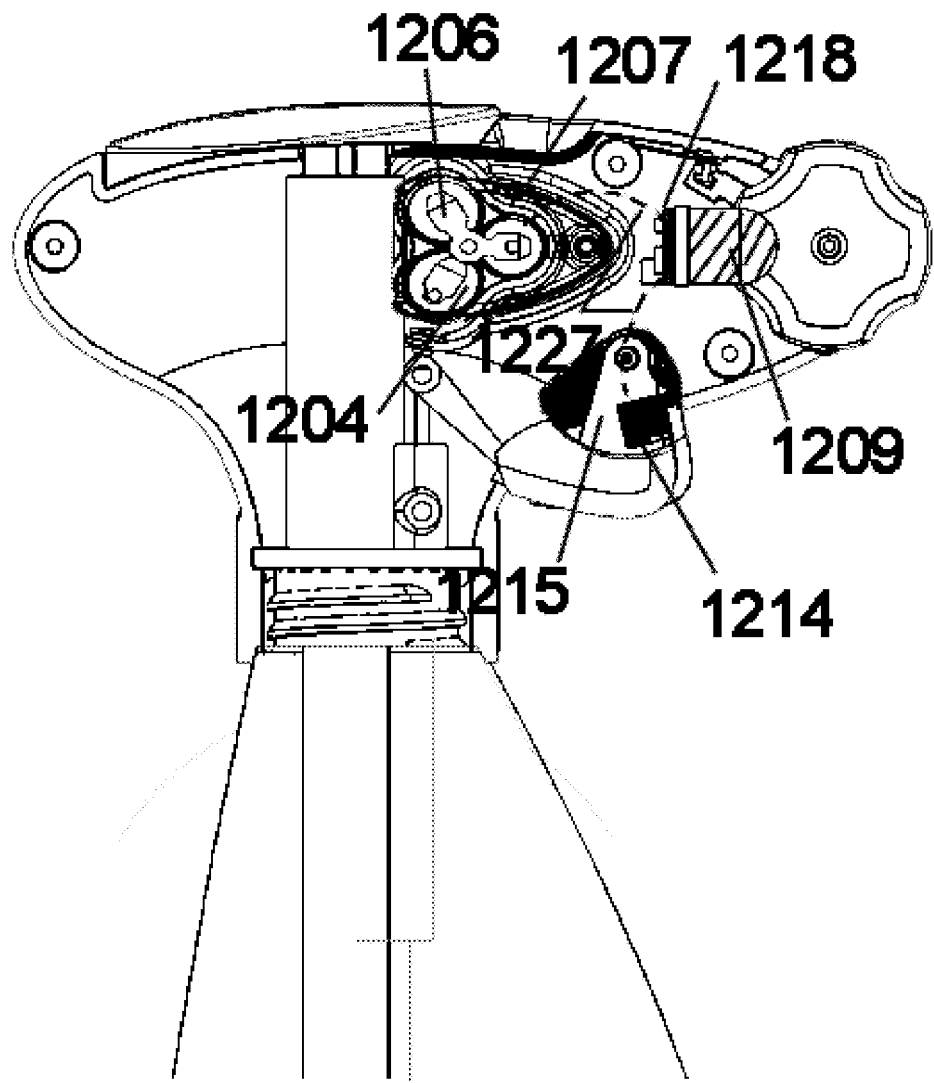
FIG. 3 is a side cross-sectional view of the electrical system in the fluid dispersal system in FIG. 1.
Figure 4:
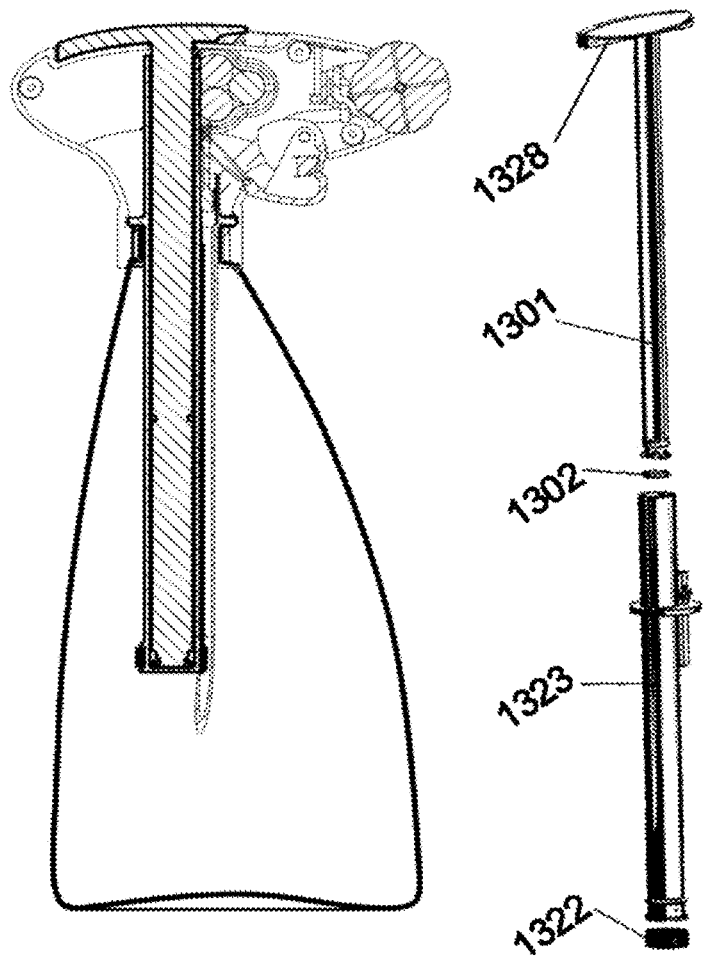

FIG. 3 is a side cross-sectional view of the electrical system 1200 in the fluid dispersal system 1000 in FIG. 2. As shown therein, the electrical system 1200 includes LED illuminators 1209 is powered by a battery cluster 1204, that may be accessed through a battery door 1207 located on the left side of the sprayer head 1100. The batteries 1204 connect to battery contacts 1206. The battery contacts 1206 connect to a circuit-board by wire 1229 then connect to an electrical switch 1214 by wire 1227. The LED illuminators 1209 are activated when the electrical switch 1214 is operated and the signal is returned by wire 1227. The user can activate the LED illuminators by pressing the electrical switch cover 1215, which in turn causes the electrical switch 1214 to move and so completes the electrical circuit between the batteries 1204 and the LED illuminators 1209. The user may press the electrical switch cover 1215 thus turning on the LED illuminators 1209, independently of spraying any fluid through the fluid distribution system 1400. The user may also press the electrical switch cover 1215 simultaneously with the action of spraying the fluid through the fluid distribution system. The simultaneous action will be explained in detail below.

In at least some embodiments, the LED illuminators 1209 are UV lights, which have various advantages over lights in visible and other portions of the electromagnetic spectrum. However, some benefits may be realized by illuminators using other than those in the ultraviolet spectrum.

FIG. 4a is a side cross-sectional view of the fluid dispersal system 1000 of FIG. 1 showing the air pressurizing pump system 1300 thereof, and FIG. 4b is an exploded isometric view of the pump system 1300 of FIG. 4a. As shown therein, the pump system 1300 includes a pump handle 1328 which is connected to a piston 1301. The pump system is used to pump air into the reservoir 1600 thus pressurizing the fluid in the reservoir 1600. The piston 1301 goes into the pump body 1323. An airtight seal is created between the piston 1301 and the pump body 1323 with a piston seal 1302. The pump body then connects to a pump valve 1322 which allows the air to enter the reservoir and pressurize the fluid.

Figure 5:
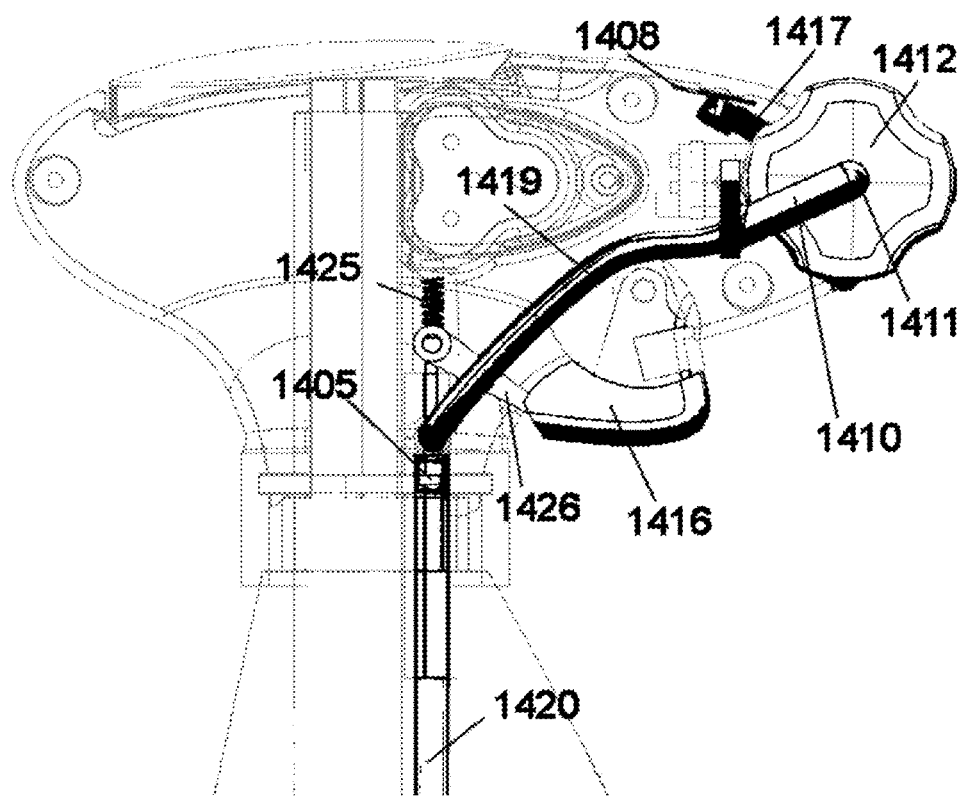
FIG. 5 is a side cross-sectional view of the fluid system in the fluid dispersal system in FIG. 1.

FIG. 5 is a side cross-sectional view of the fluid system 1400 in the sprayer system in FIG. 1. As shown therein, the fluid system 1400 includes a selectable nozzle 1412 that allows the user to choose the type of spray stream and the volume of spray. In this preferred embodiment, the selectable nozzle 1412 contains four different settings. In other preferred embodiments the selectable nozzle 1412 may have less than four settings or more than four settings. In this preferred embodiment the selectable nozzle 1412 is connected to a mode indicator 1408 via an indicator linkage 1417. The mode indicator 1408 contains writing or an icon to show the specific setting the user has chosen when they turn the selectable nozzle 1412. In other preferred embodiments a mode indicator 1408, may not exist. Also, in some embodiments the drawing or words may be placed directly on the selectable nozzle 1412 to indicate the setting.

The selectable nozzle 1412 is also connected to a fluid channel 1410 via a channel gasket 1411. The fluid channel 1410 connects to a valve 1405 and the valve 1405 connects to a dip tube 1420. The valve 1405 also connects to a lever 1426, and a spring 1425. When the lever 1426 pushes up on the spring 1425, the valve 1405 is opened. In order to open the valve the user must push the fluid valve switch 1416, causing the lever 1426 to push up on the spring 1425, thus opening the valve 1405.

When fluid in the reservoir is pressurized by the pump system 1300, the pressure in the reservoir forces the fluid into the dip tube 1420. In turn, when the user pushes on the fluid valve switch 1416, the valve 1405 opens, and the pressure in the system forces fluid into the fluid channel and finally out the selectable nozzle 1412. In other preferred embodiments the fluid system 1300 may be controlled by a fluid pump instead of a pressurized pump system.

Figure 6:
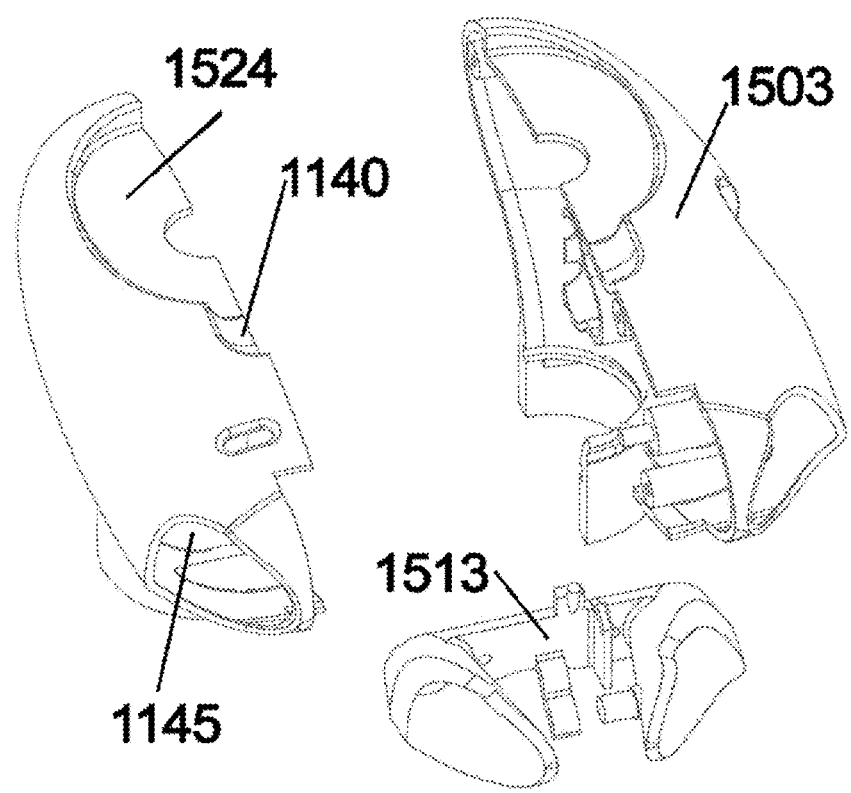
FIG. 6 is an exploded isometric view of the sprayer enclosure of FIG. 1.

FIG. 6 is an exploded isometric view of the enclosure components 1500 of the fluid dispersal system 1000 in FIG. 2. As shown herein, the sprayer head includes at least three enclosure components, including a left housing 1503, a right housing 1524, and a light fairing 1513. The left and right housing 1503,1524 keep all of the parts of the electrical system 1200, pump system 1300, and fluid system 1400 in place. The light fairing 1513 protects the LED illuminators 1209 as well as provides light holes 1145 for the light to shine out of the sprayer. The light fairing 1513 also holds the selectable nozzle 1412 and fluid channel 1410 in place, since it is partially on the exterior of the housing 1503, 1524. The light fairing also provides an axle and slide surface for the mode indicator component 1408, and indicator linkage 1417 in one embodiment.

Figure 7:
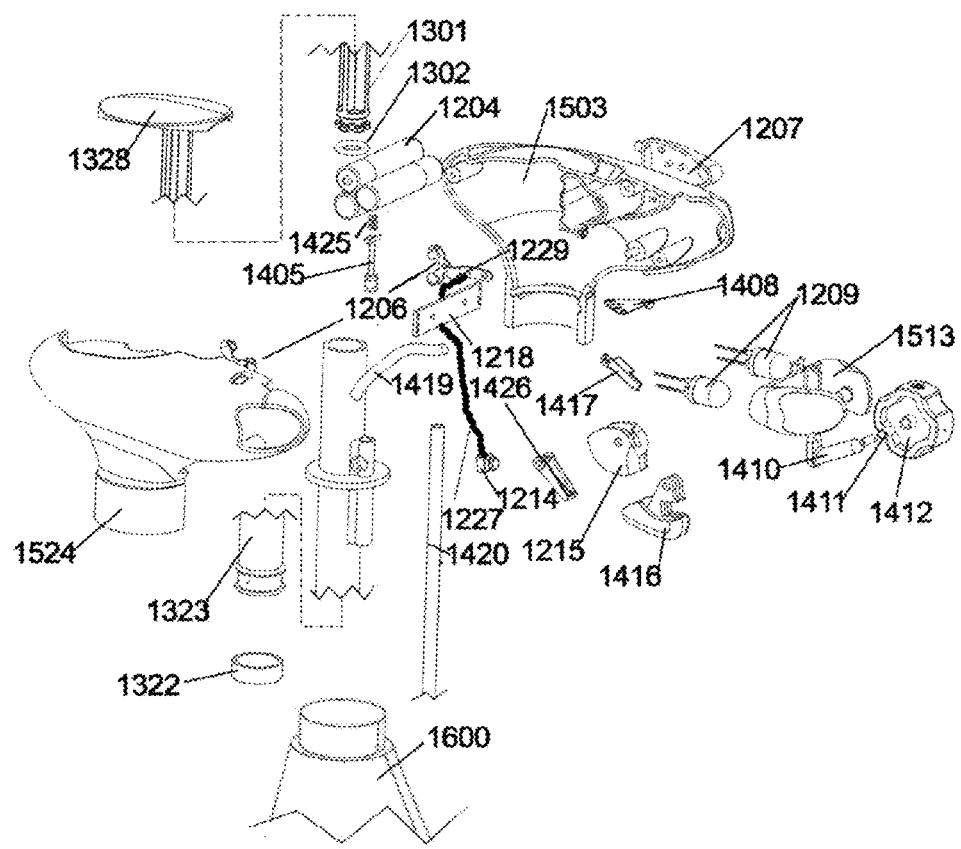
FIG. 7 is an exploded isometric view of the sprayer assembly of FIG. 1.

FIG. 7 is an exploded isometric view of the fluid dispersal system 1000 of FIG. 1. FIG. 7 shows a detail view of the parts described in FIGS. 3-6. As shown therein, the fluid dispersal system 1000 includes a pump handle 1328, a piston 1301, a piston seal 1302, a left housing 1503, a battery cluster 1204, a valve 1405, battery contacts 1206, a battery door 1207, a mode indicator 1408, LED illuminators 1209, a fluid channel 1410, a channel gasket 1411, a selectable nozzle 1412, a light fairing 1513, an electrical switch 1214, an electrical switch cover 1215, a fluid valve switch 1416, an indicator linkage 1417, a circuit board 1218, a fluid tube 1419, a dip tube 1420, a reservoir 1600, a pump valve 1322, a pump body 1323, a right housing 1524, a spring 1425, a lever 1426, wires 1227,1229, and a pump handle 1328.

Figure 8:
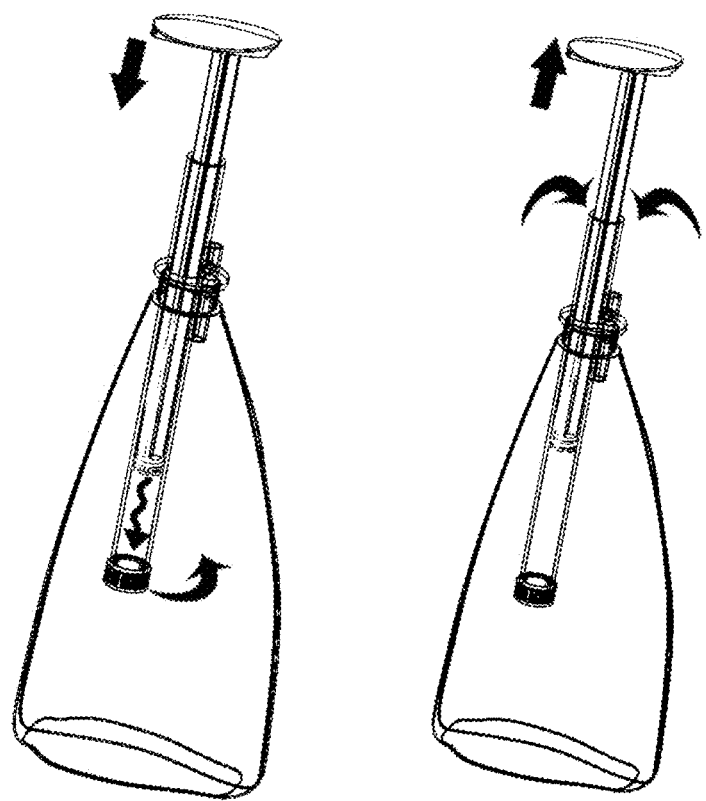
FIG. 8 is a diagram of the air pump operation used to pressurize the system.

FIG. 8 is a diagram of the air pump system in accordance with a preferred embodiment of the present invention in which the pump handle 1328, which is attached to the piston 1301 and piston seal causes air to move past the piston when pulled, and air to be compressed toward the base of the pump body 1323, being forced out the pump valve 1322 and causing the reservoir 1600 to be pressurized.

Figure 9A:
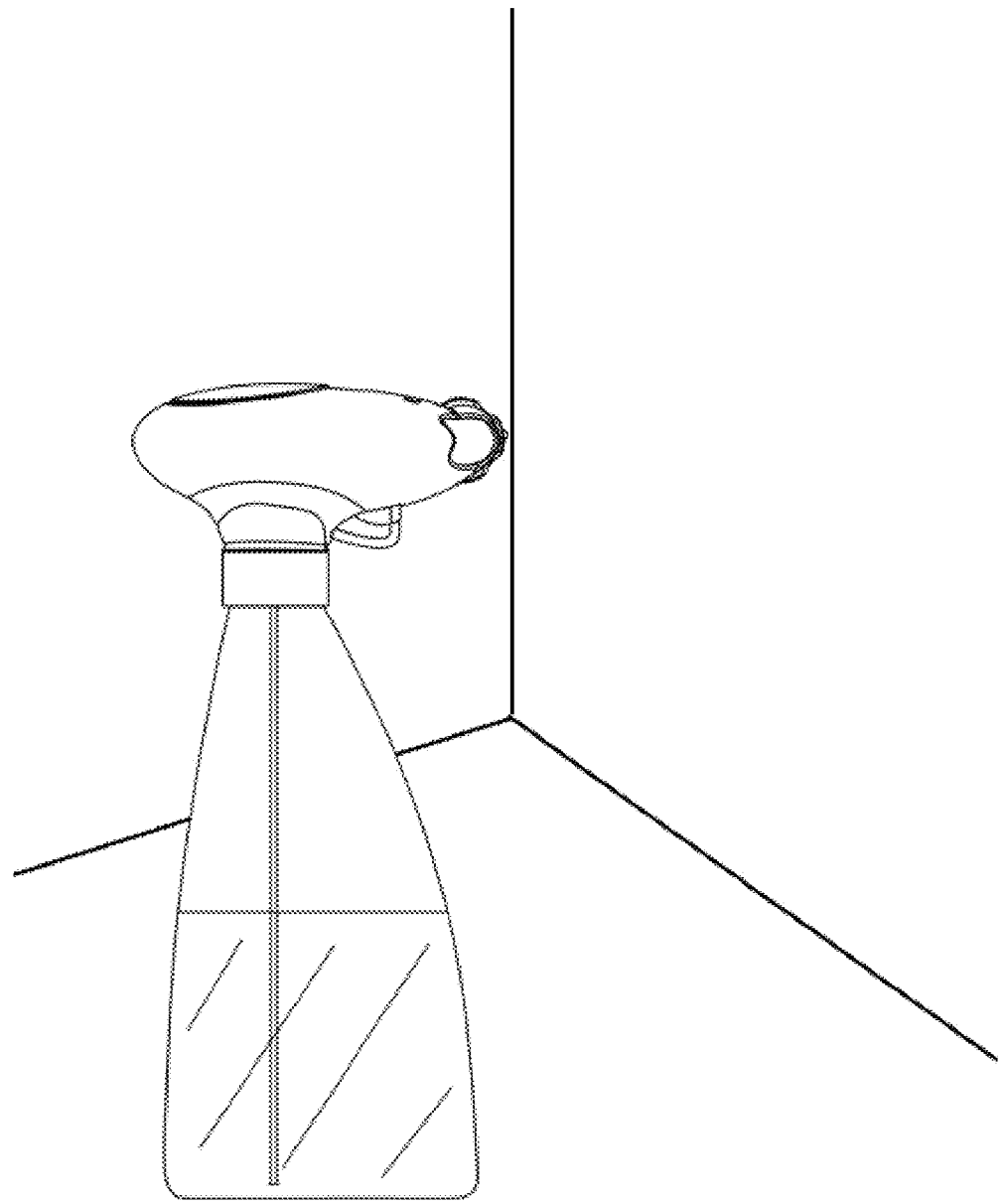
FIGS. 9A-9D are partially schematic side views of the fluid dispersal system of FIG. 1, illustrating its use.
Figure 9B:
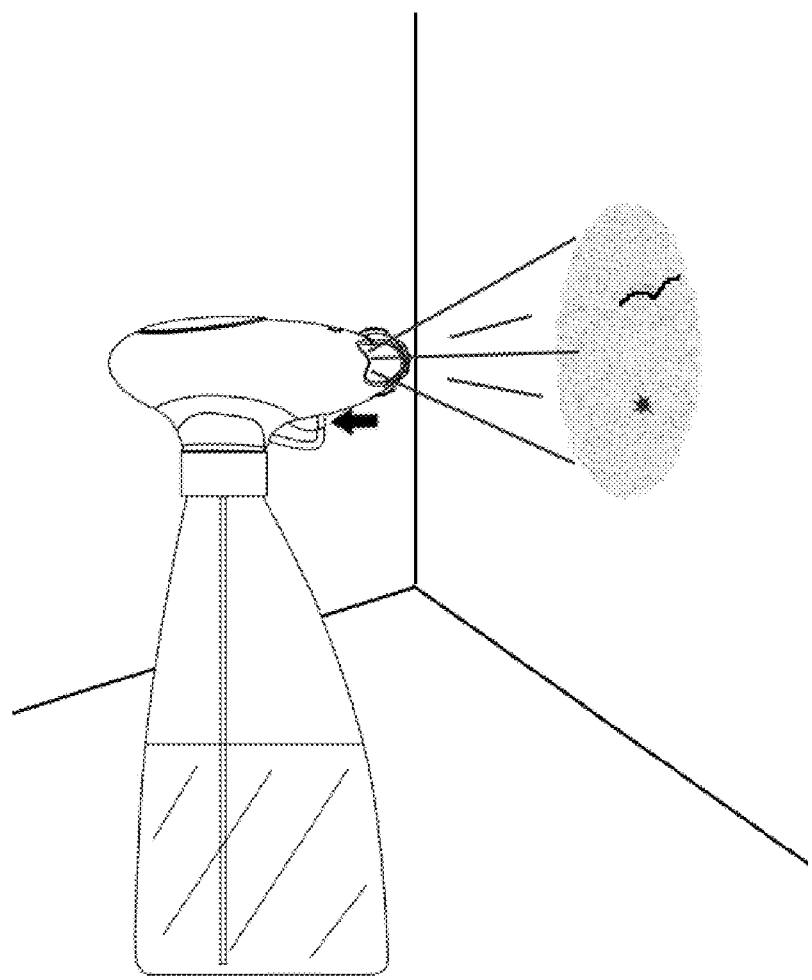
Figure 9C:
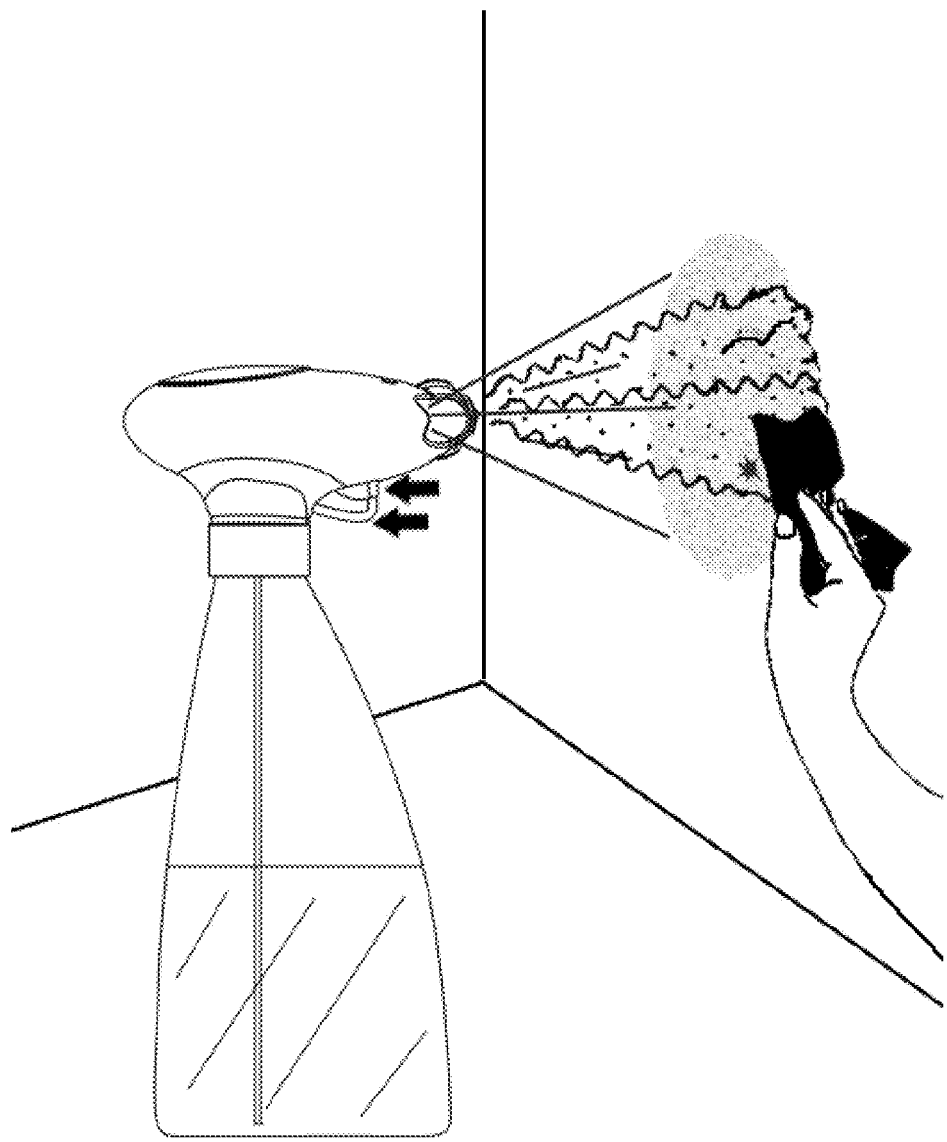
Figure 9D:
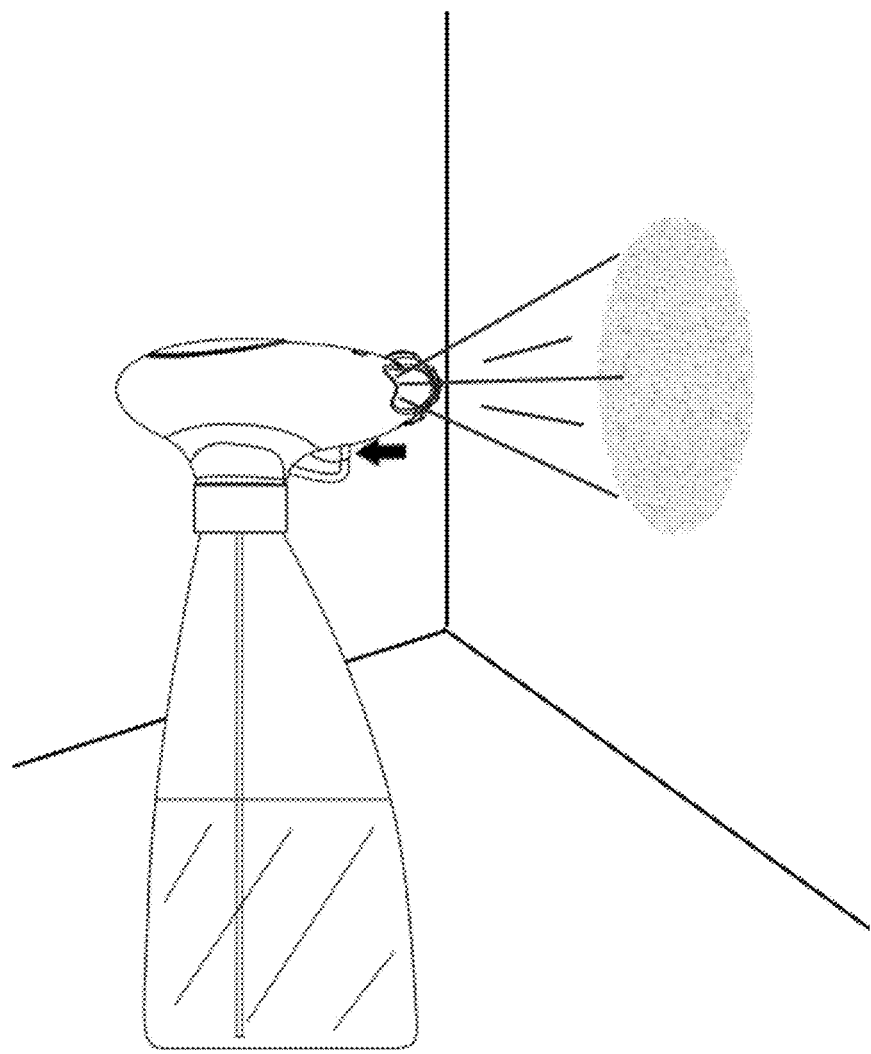

FIGS. 9A-9D are partially schematic side views of the fluid dispersal system 1000 of FIG. 1, illustrating its use. FIGS. 9A-9D illustrate the use of the present invention in four steps: FIG. 9A illustrates a room with no observed contaminants; FIG. 9B illustrates activation of ultraviolet LED illuminators, in at least some embodiments, revealing overlooked contaminants which auto-fluoresce; FIG. 9C illustrates dispensing of fluid to the contaminants and cleaning of the previously invisible contaminants; and FIG. 9D illustrates inspection of the area using ultraviolet lighting to reveal contaminants removed.

Figure 10:
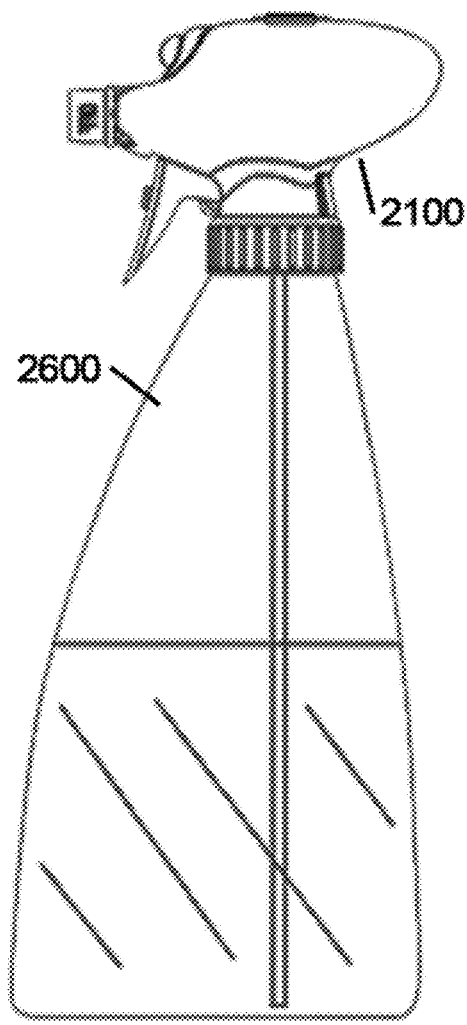
FIG. 10 is a side view of a lighted, pump actuated, fluid dispersal system in accordance with a second preferred embodiment of the present invention.
Figure 11:
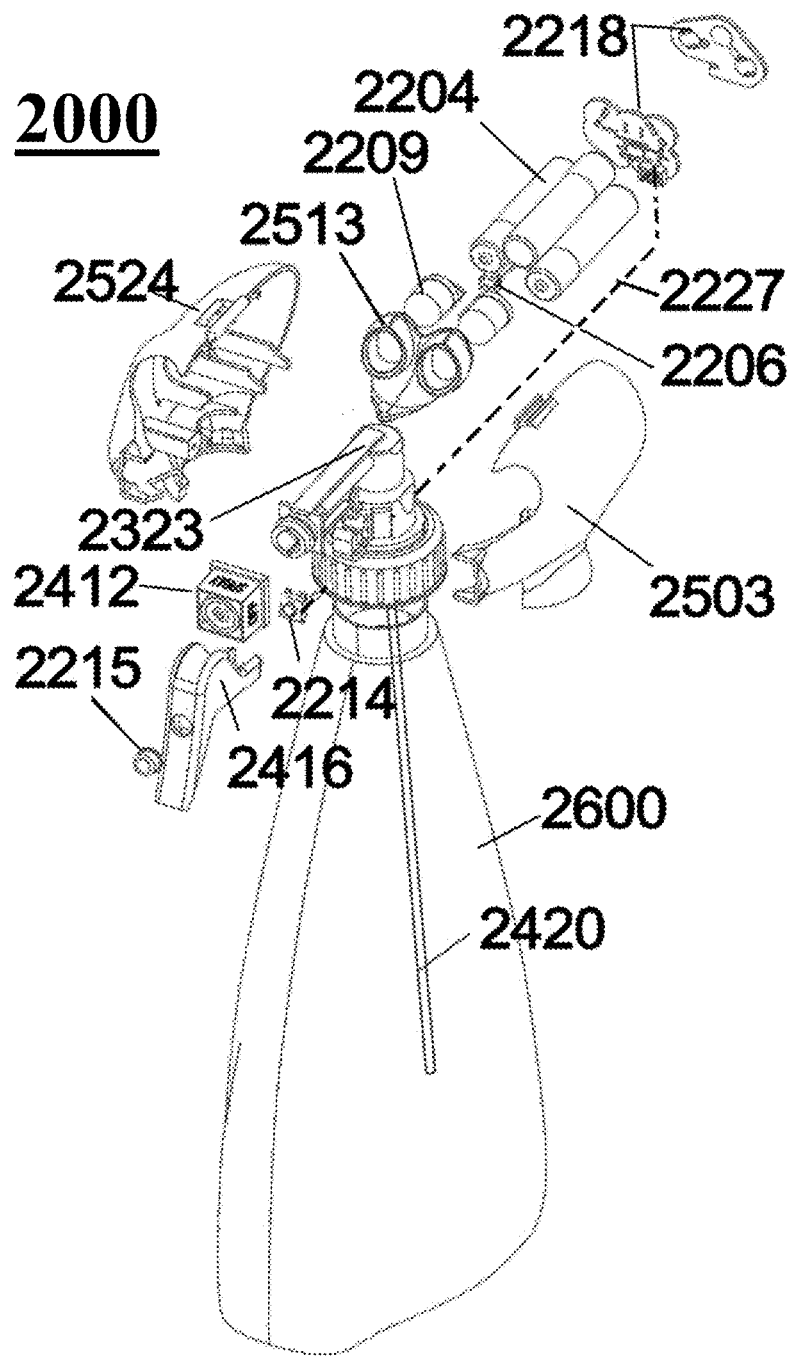
FIG. 11 is an exploded view of the fluid dispersal system of FIG. 10.

FIG. 10 is a perspective view of a lighted pump actuated fluid dispersal system 2000 in accordance with a second preferred embodiment of the present invention; and FIG. 11 is an exploded view of the fluid dispersal system of FIG. 10. The fluid dispersal system 2000 of FIGS. 10 and 11 is somewhat similar to the fluid dispersal system 1000 described in detail above in FIGS. 1-9 and includes contains a sprayer head 2100 and a reservoir 2600, but does not contain an air pressurizing pump system 1300 and also has fewer parts in the fluid distribution system. The fluid distribution system include a selectable nozzle 2412, and a fluid valve switch 2416 which operates the same way as a standard trigger found on spray bottles operates.

The enclosure components are also somewhat similar to those found in the fluid dispersal system 1000 shown in FIGS. 1-7. The components include a left housing 2503, a right housing 2524, and a light fairing 2513.

Figure 12:
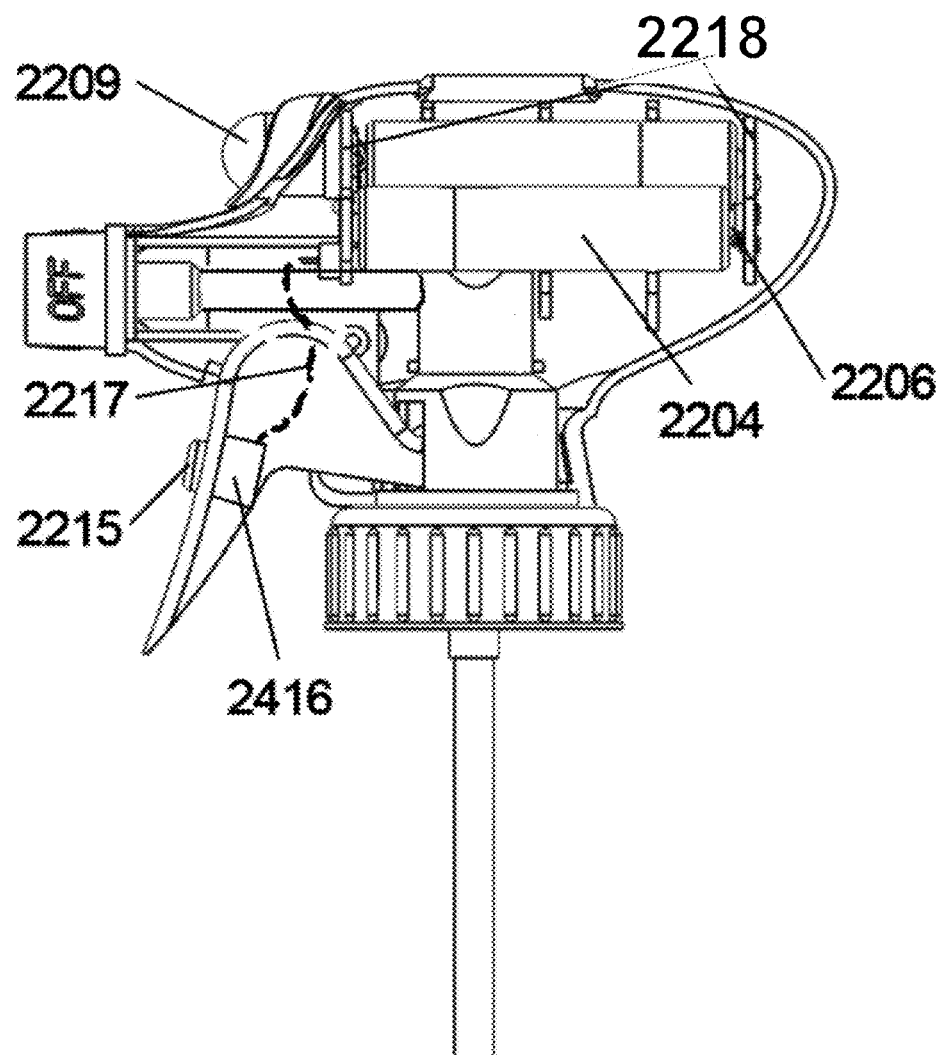
FIG. 12 is a sectioned side view of the sprayer head of FIG. 10 illustrating the electrical component layout of the fluid dispersal system.

FIG. 12 is a sectioned side view of the sprayer head 2100 of FIG. 10 illustrating the electrical component layout of the fluid dispersal system 2000. The electrical system contains batteries 2204, LED illuminators 2209, battery contacts 2206, a circuit board 2218 an electrical switch 2214, and an electrical switch cover 2215. The user operates the electrical system similarly to the electrical system 1200. The user presses the electrical switch cover 2215 to turn on the LED illuminators 2209. The user may press the electrical switch cover 2215 at the same time as spraying the fluid or independently of spraying the fluid.

Figure 13:
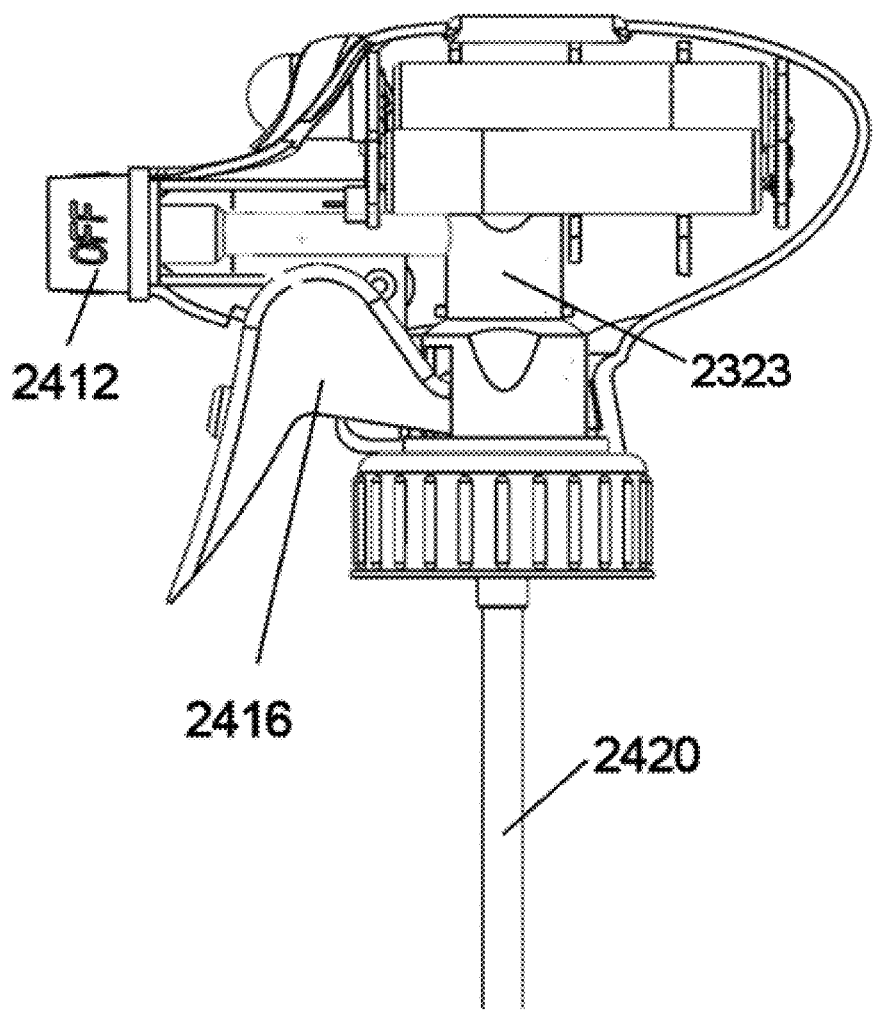
FIG. 13 is a sectioned side view of a illustrating the fluid component layout of the fluid dispersal system of FIG. 10.

FIG. 13 is a sectioned side view of the sprayer head of FIG. 10 illustrating the pump system 2200 of the fluid dispersal system of FIG. 10. The pump system 2200 utilizes a standard trigger operated piston pump. A trigger 2416 is manually operated and raises an internal piston within the standard trigger sprayer pump 2323, this draws fluid up the dip tube 2420 and forces it out through the nozzle 2412.

Figure 14:
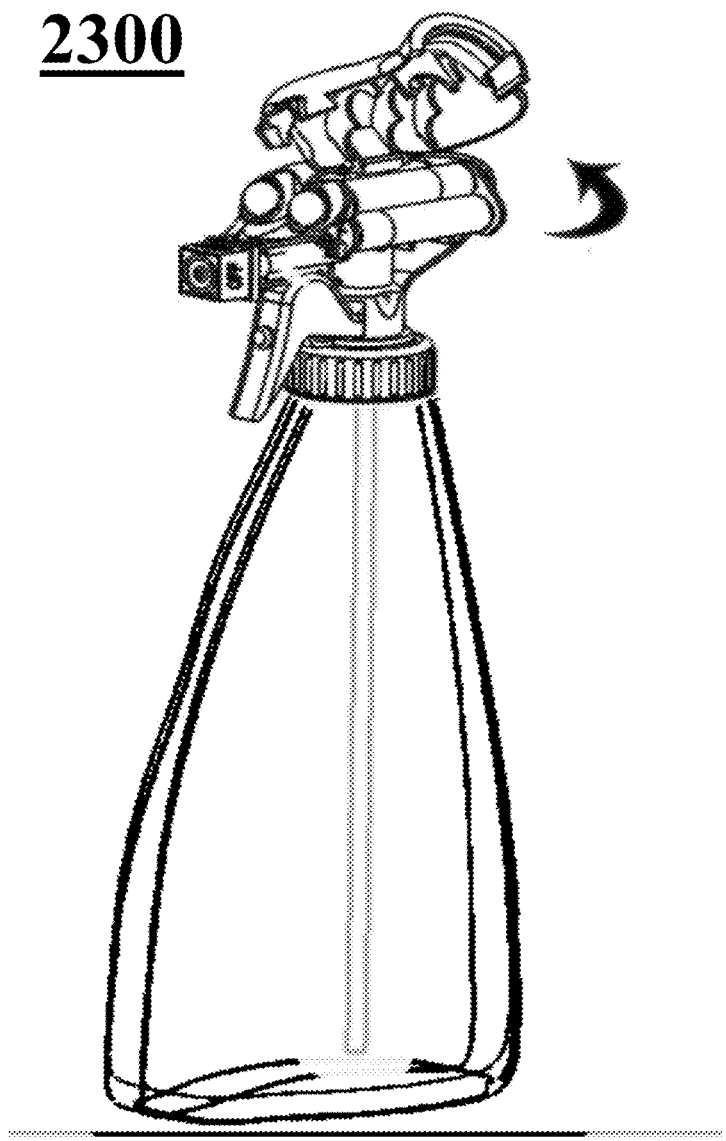
FIG. 14 is a diagram illustrating the enclosure opening method of the fluid dispersal system of FIG. 10.

FIG. 14 is a diagram illustrating the enclosure opening method 2300 of the fluid dispersal system of FIG. 10. This preferred embodiment features a hinged enclosure that allows easy access to the batteries for replacement, and simple manufacturing assembly to install the conventional sprayer pump as well as other components.

Figure 15A:
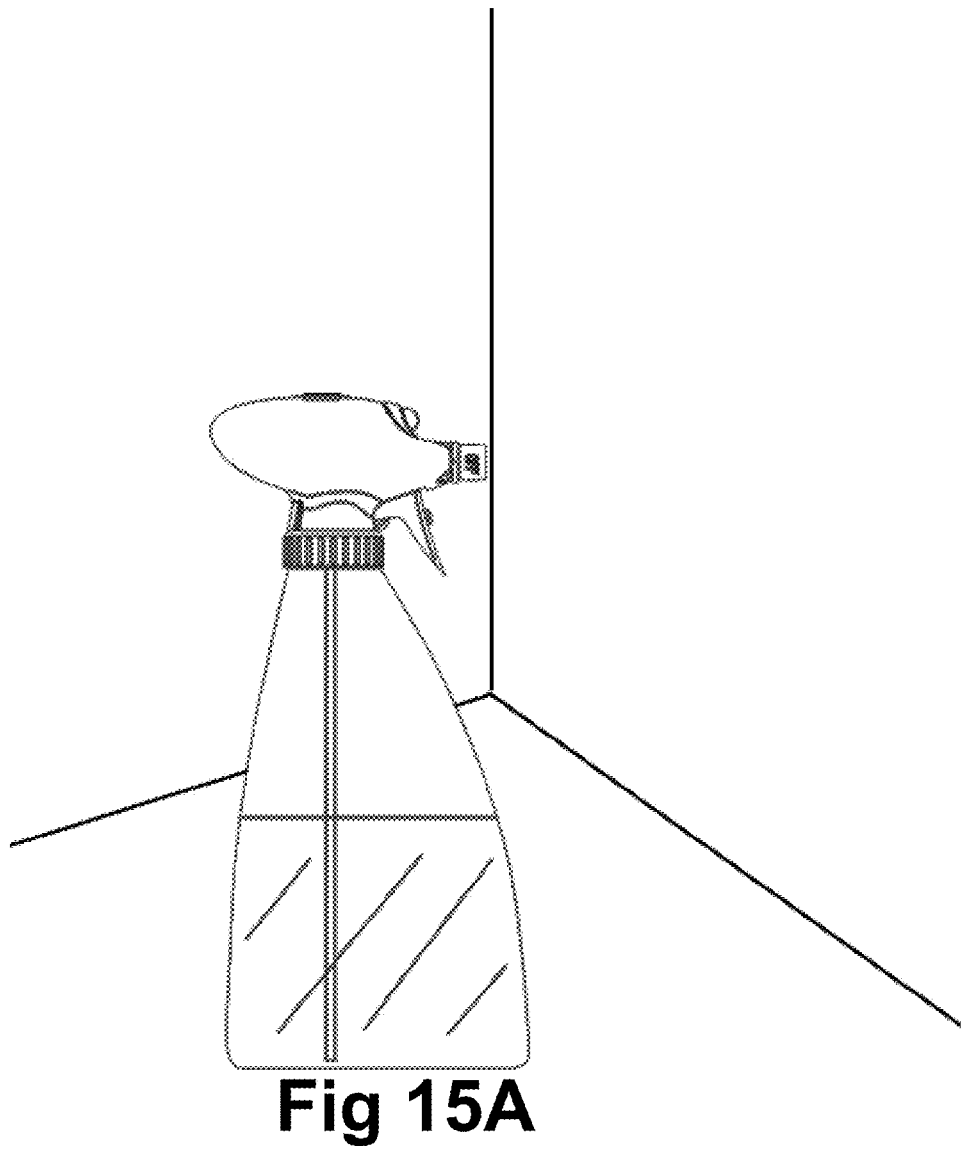
FIGS. 15A-15D are partially schematic side views of the fluid dispersal system of FIG. 10, illustrating its use.
Figure 15B:
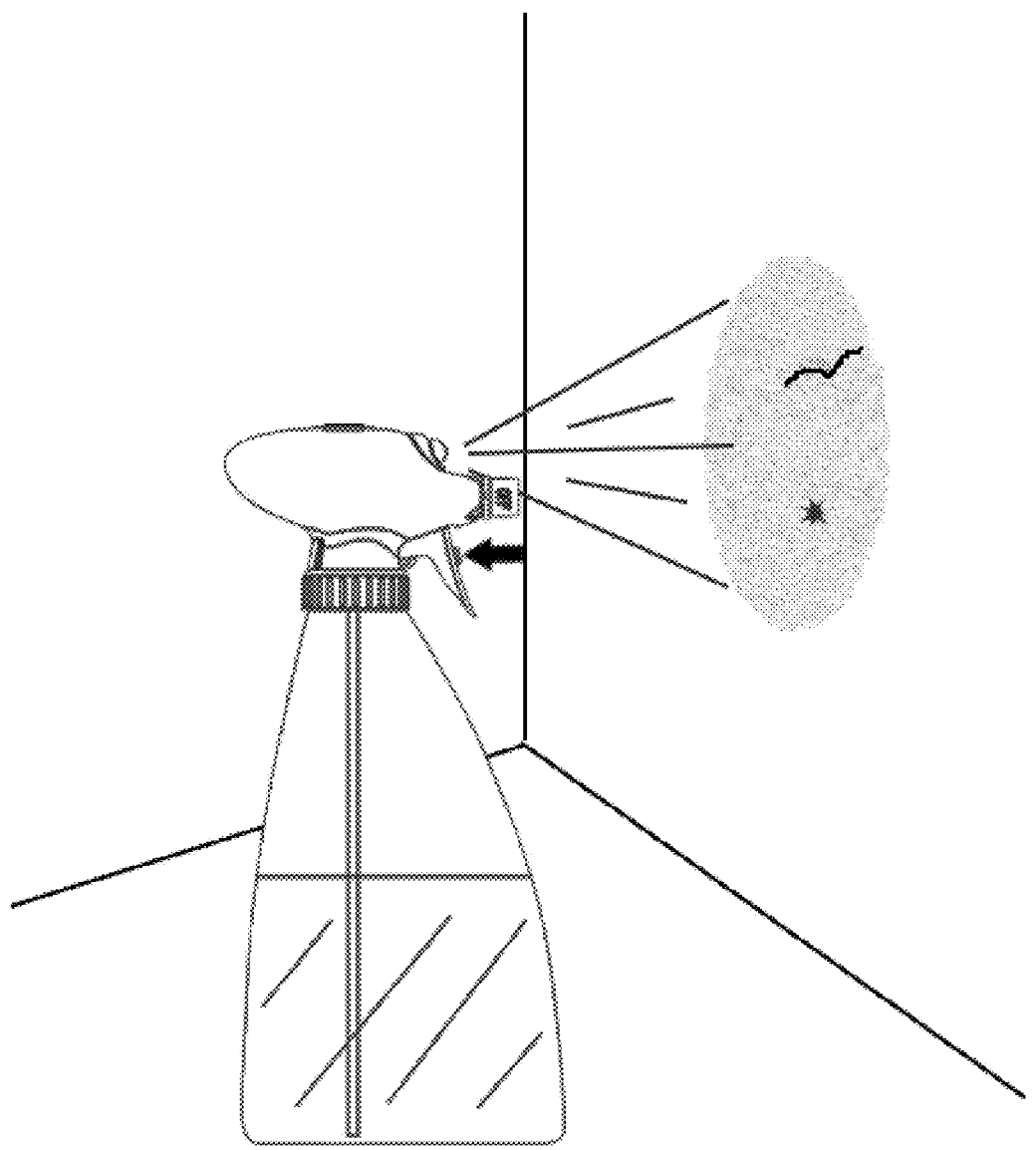
Figure 15C:
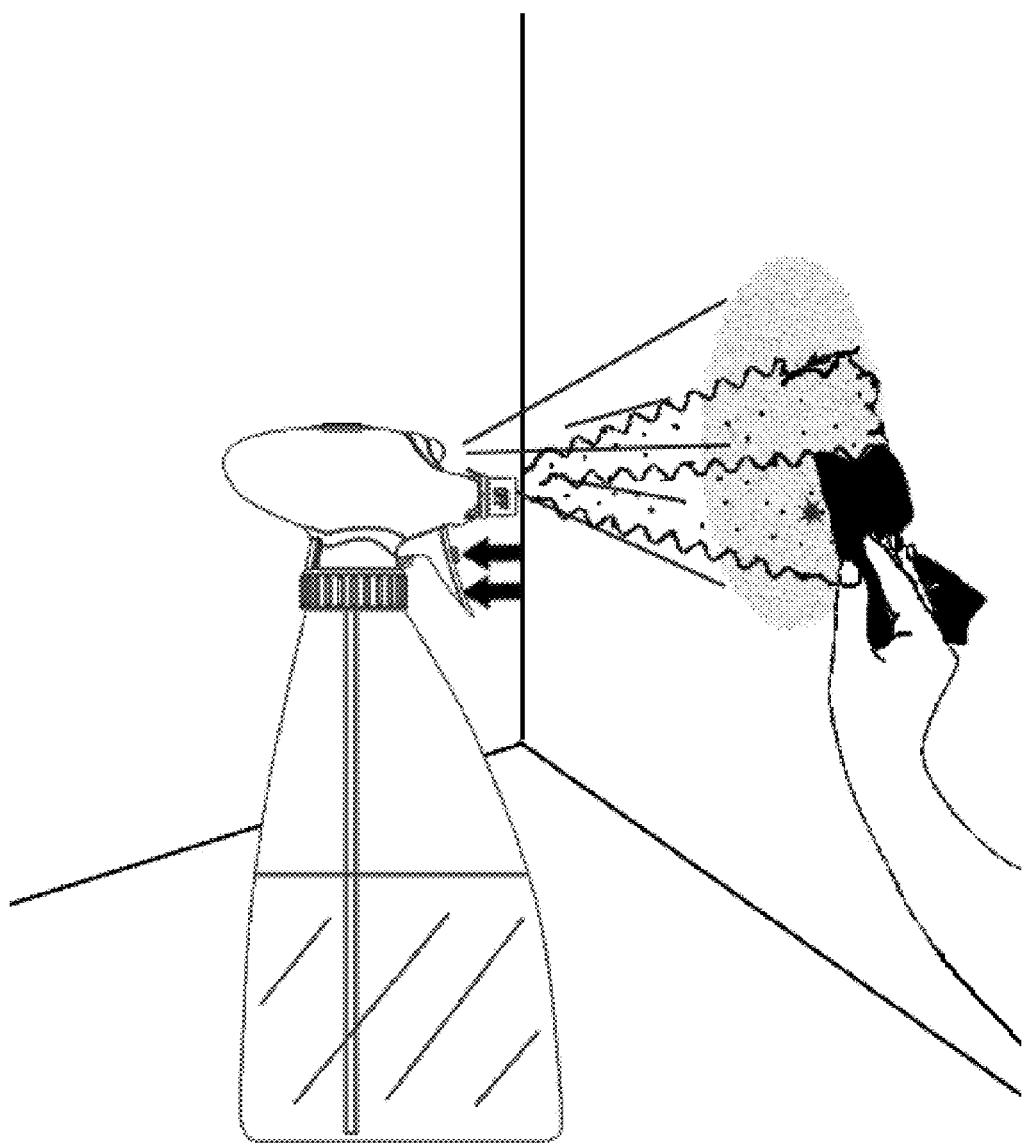
Figure 15D:
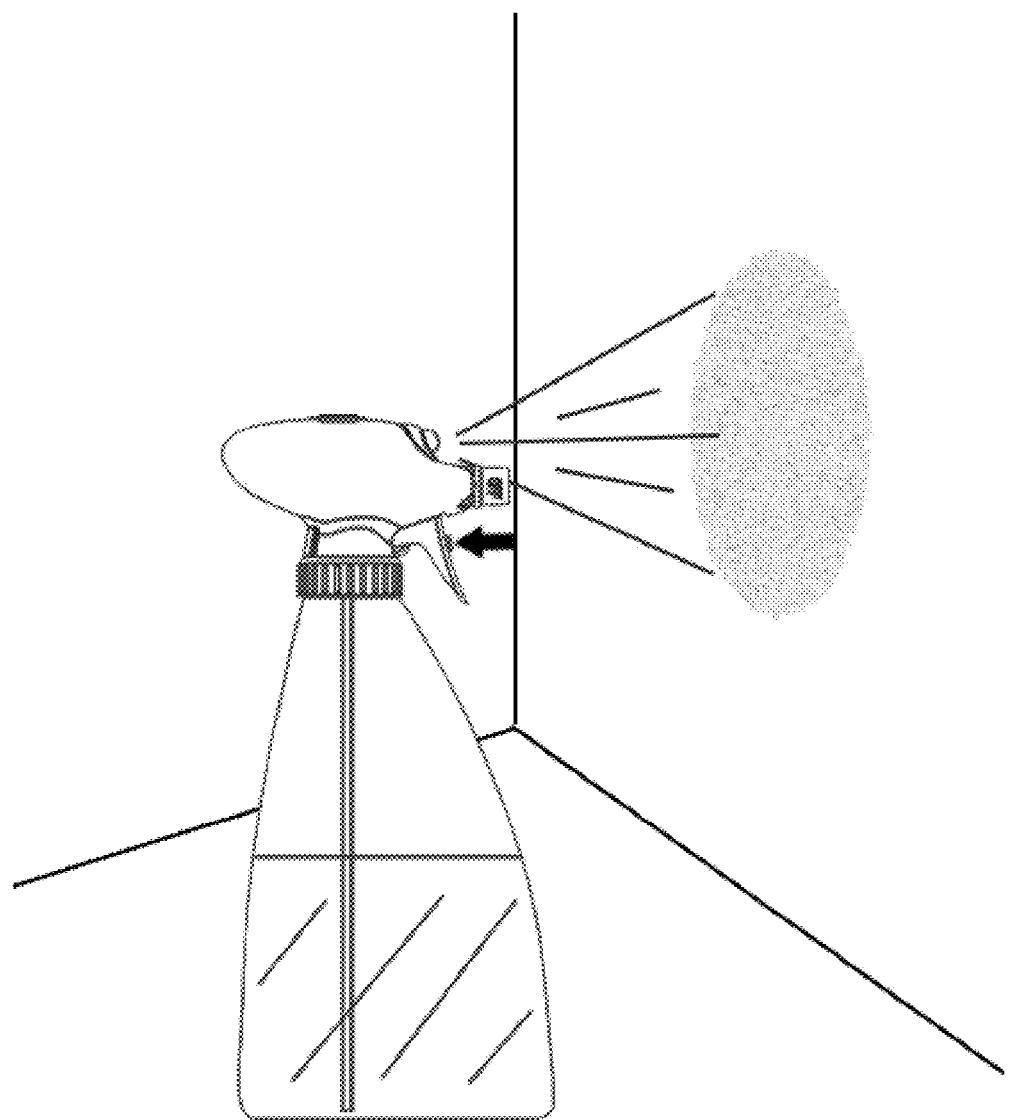

FIGS. 15A-15D are partially schematic side views of the fluid dispersal system 2000 of FIG. 10, illustrating its use. FIGS. 15A-15D illustrate the use of the present invention in four steps: FIG. 15A illustrates a room with no observed contaminants, FIG. 15B illustrates activation of the LED illuminators revealing previously unobserved contaminants, FIG. 15C illustrates dispensing of fluid to the contaminants and cleaning of the observed contaminants, and FIG. 15D illustrates inspection of the area with contaminants removed.

Figure 16:
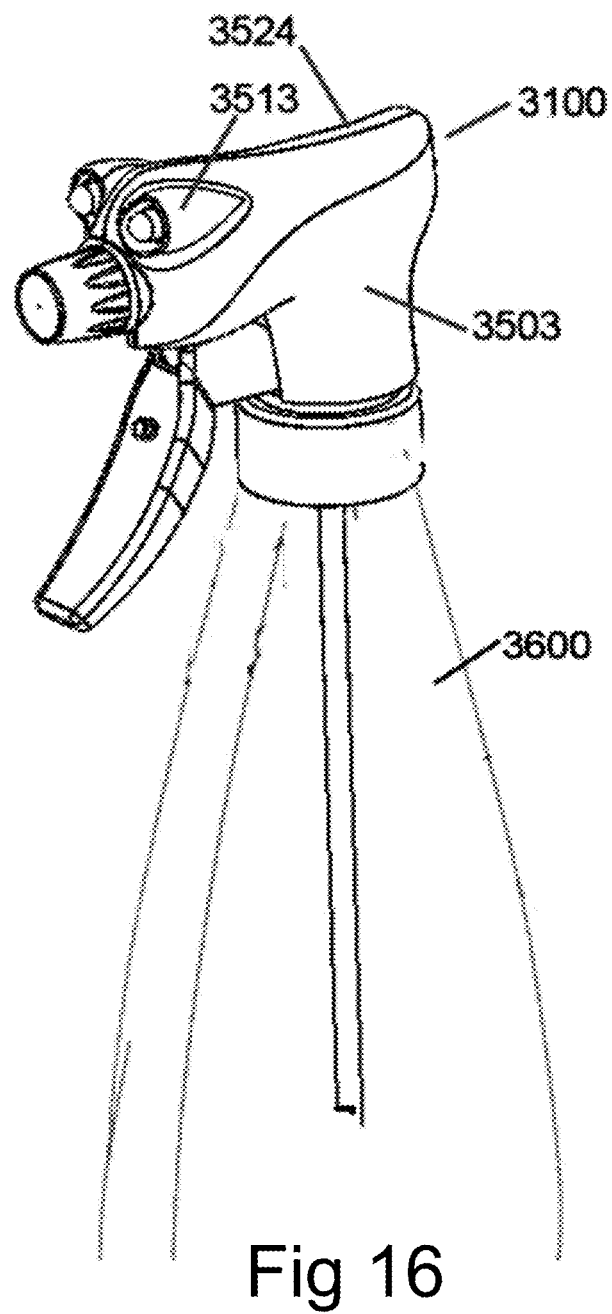
FIG. 16 is a front isometric view of a lighted, pump actuated, fluid dispersal system in accordance with a third preferred embodiment of the present invention.
Figure 17:
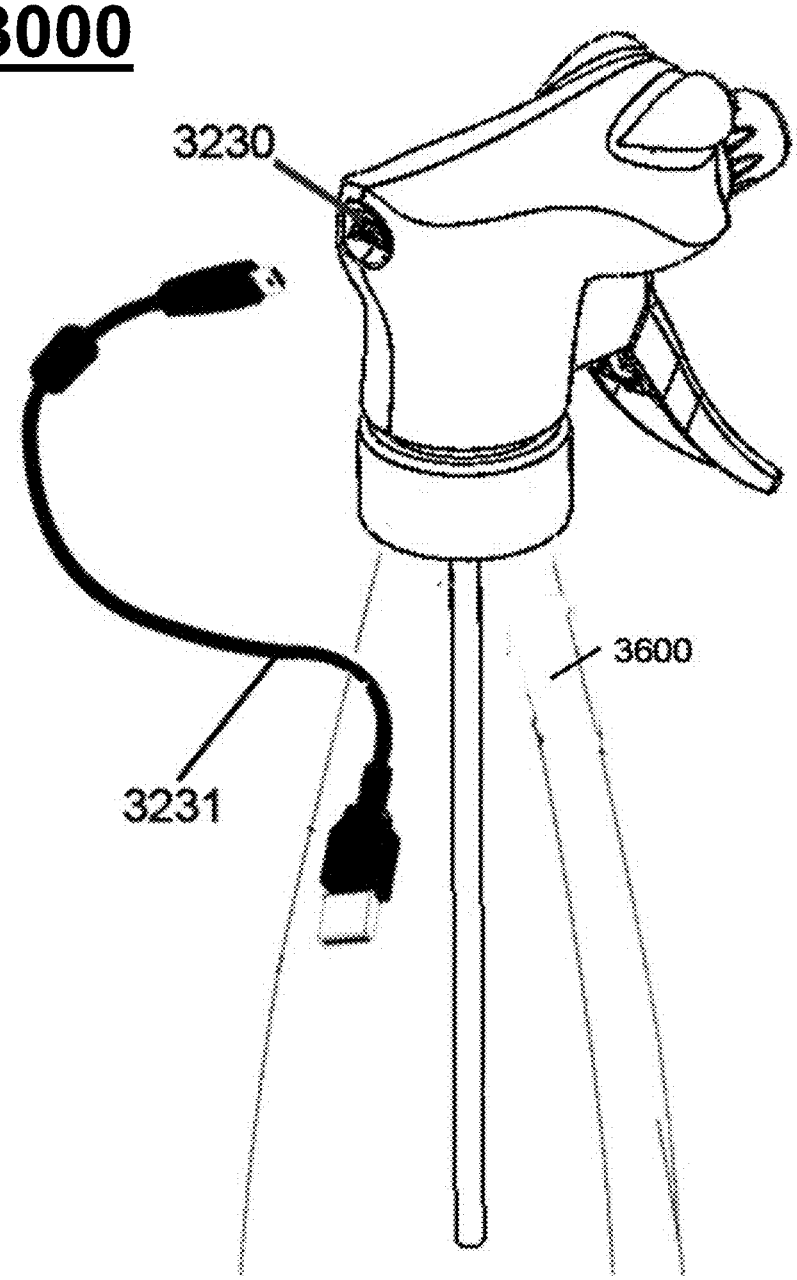
FIG. 17 is a rear isometric view of the fluid dispersal system of FIG. 16 illustrating an accessory.

FIG. 16 is a front isometric view of a lighted, pump actuated, fluid dispersal system 3000 in accordance with a third preferred embodiment of the present invention, and FIG. 17 is a rear isometric view of the fluid dispersal system 3000 of FIG. 16 illustrating an accessory. The fluid dispersal system 3000 of FIGS. 16 and 17 is somewhat similar to the fluid dispersal system 1000 described with regard to FIGS. 1-9 and includes a sprayer head 3100 and a reservoir 3600. The sprayer head 3100 includes an enclosure having a left side 3503, a right side 3524, and a light fairing 3513. However, the fluid dispersal system 3000 of FIGS. 16 and 17 does not contain an air pressurizing pump system 1300 and also has fewer parts in the fluid distribution system. It also utilizes a rechargeable battery 3204, it can be recharged via standard miniature Universal Serial Bus (USB) cable 3231, and it contains a rotary adjustable spray nozzle 3412.

Figure 18:
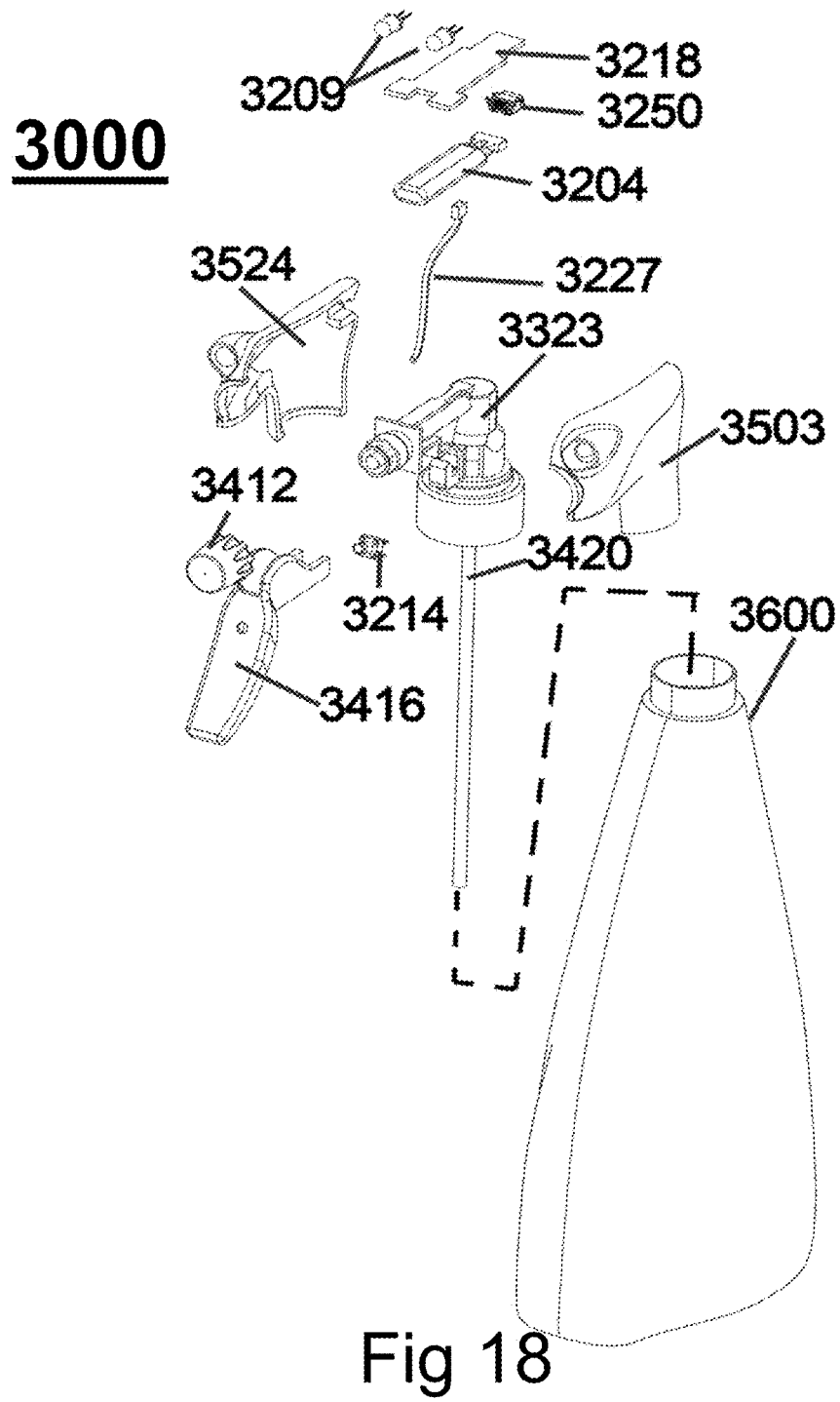
FIG. 18 is an exploded isometric view of the fluid dispersal system of FIG. 16.

FIG. 18 is an exploded isometric view of the fluid dispersal system 3000 of FIG. 16. The fluid dispersal system 3000 includes LED illuminators 3209, a circuit-board 3218, a mini USB charging port 3250, a rechargeable battery 3204, a wire connection to the switch 3227, a right enclosure 3524, a conventional trigger operated pump assembly 3323, a left enclosure 3503, a rotary adjustable nozzle 3412, an electrical trigger switch 3214, a trigger lever 3416, a dip tube 3420, and a reservoir 3600.

In general, the complete sprayer assembly operates the same way as previously documented versions with the exception of a consolidated circuit-board layout and charging features.

Figure 19:
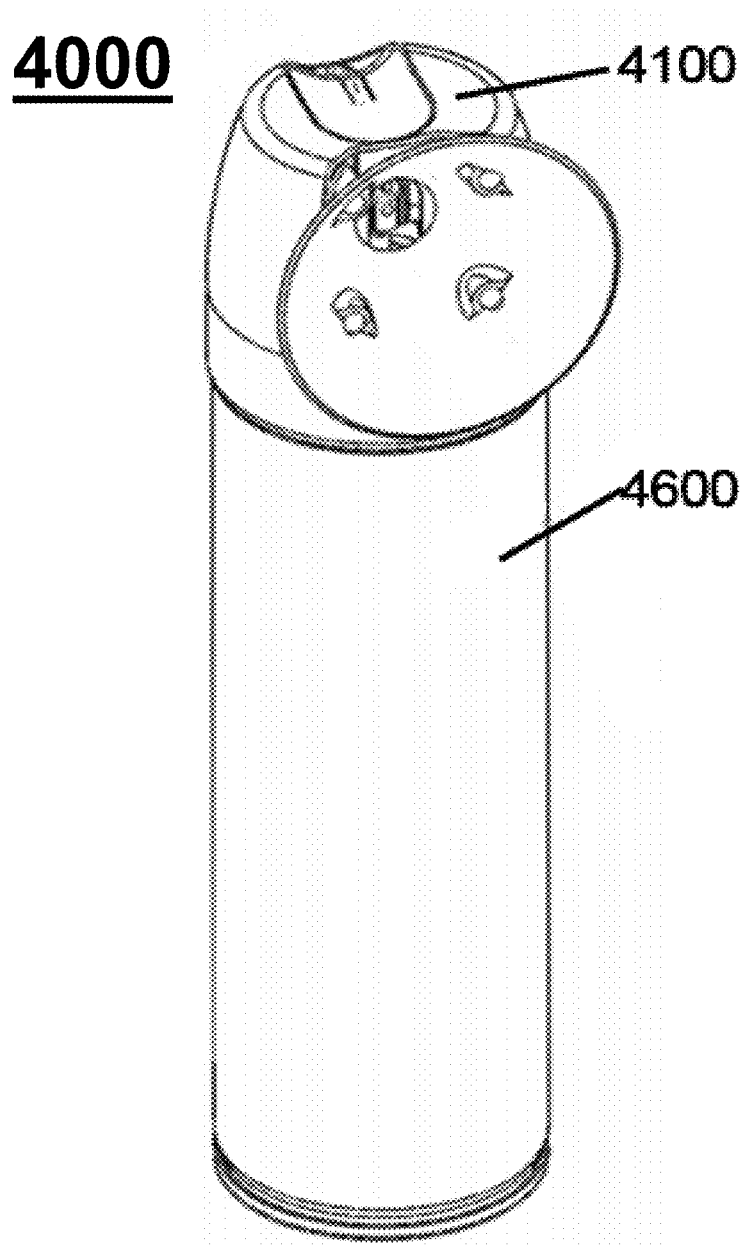
FIG. 19 is an isometric view of a lighted, valve actuated, fluid dispersal system in accordance with a fourth preferred embodiment of the present invention.

FIG. 19 is an isometric view of a lighted, valve actuated, fluid dispersal system 4000 in accordance with a fourth preferred embodiment of the present invention. The fluid dispersal system 4000 of FIG. 19 is an aerosol variation which may be realized either as a complete assembly, or as a universal or modular sprayer head 4100 with electrical lighting features.

Figure 20:
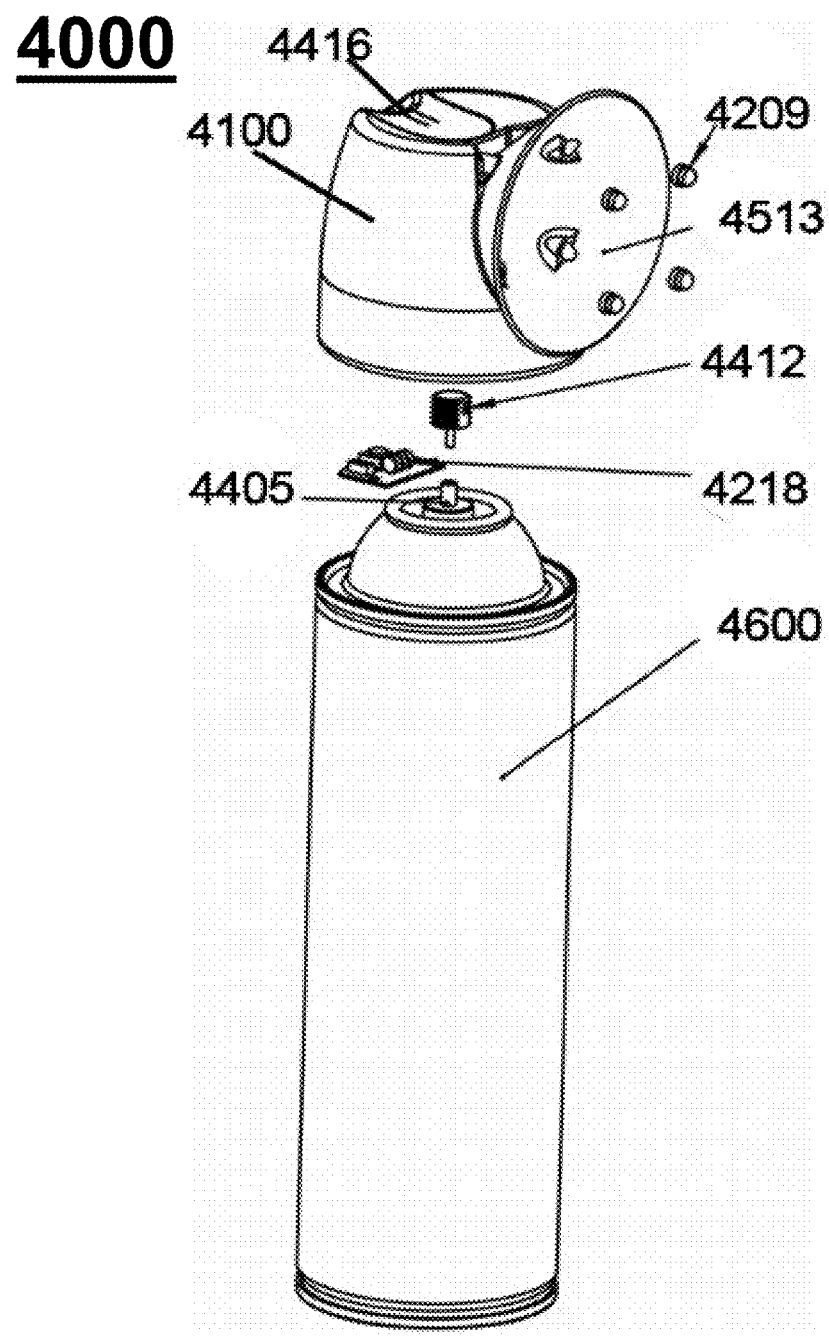
FIG. 20 is an exploded isometric view of the lighted, valve actuated, fluid dispersal system of FIG. 19.

FIG. 20 is an exploded isometric view of the lighted, valve actuated, fluid dispersal system 4000 of FIG. 19. The fluid dispersal system 4000 of FIGS. 19 and 20 contains LED illuminators 4209, a circuit-board 4218 which consolidates batteries and an integrated electrical switch onto the circuit-board, a valve operated dispensing method 4405, a manually operated nozzle 4412, a light fairing component 4513, a gas filled canister 4600, and a button cover 4416. The usage and operational method is similar to previously described embodiments with the exception that it is lacking a pump, and instead utilizes a consumable pressurized gas and valve as a means of dispensing.

In at least some embodiments, one or more of the fluid dispersal systems described herein may utilize button type batteries and/or a rechargeable battery or batteries.

In at least some embodiments, one or more of the fluid dispersal systems described herein may utilize a transparent light channel or channels.

In at least some embodiments, one or more of the fluid dispersal systems described herein may utilize an integrated trigger switch whereby a partial pull of the trigger automatically engages the lighting element or elements.

In at least some embodiments, a LED illuminator switch is integrated into the switch causing illumination when the trigger is partially pulled.

In at least some embodiments, the sprayer head is a modular component suitable to fit either a common size reservoir or a custom replaceable reservoir.

In at least some embodiments, one or more of the fluid dispersal systems described herein may utilize glow-in-the-dark material which is charged by the illumination to improve visibility or indicate modes. In at least some of these embodiments, the light fairing component is phosphorescent and aids in illuminating mode status and user experience.

In at least some embodiments, the battery compartment is hinged from the rear of the enclosure for convenient access.

In at least some embodiments, plastic light piping material is utilized to allow use of surface mount components or more convenient or desirable lighting configurations.

In at least some embodiments, one or more of the fluid dispersal systems described herein may utilize a separate sprayer head that may attach to a particular reservoir or replaceable cartridge or reservoir. A reservoir interface that removably connects the sprayer head to the reservoir may be provided for this purpose.

In at least some embodiments, one or more of the fluid dispersal systems described herein may utilize a separate sprayer head that is designed to attach to a standard or custom pressurized gas aerosol container.

Based on the foregoing information, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements; the present invention being limited only by the claims appended hereto and the equivalents thereof.

What is claimed is:

1. A fluid dispersal system with integrated UV lighting, comprising:
    a reservoir of non-pressurized cleaning and sanitizing fluid;
    a sprayer head removably and replaceably connected to the fluid reservoir;
    a nozzle, supported by, and removable with the sprayer head and in fluid communication with the reservoir, to disperse fluid from the reservoir in a spray direction;
    a pump system that supplies the fluid from the reservoir to the nozzle;
    an ultraviolet lighting element, supported by the sprayer head adjacent the spray nozzle, that directs non-focused ultraviolet light in a direction generally parallel to the spray direction to illuminate an area of a surface and identify contaminants on the surface area to be cleaned;
    an actuator; and
    an electrical switch to activate the ultraviolet lighting element;
    wherein actuation of the electrical switch is linked mechanically to actuation of the fluid dispersal.

2. The fluid dispersal system of claim 1, wherein the pump system includes a trigger operated piston pump wherein a manually-operated trigger raises an internal piston to draw fluid up a dip tube and force it out through the nozzle.

3. The fluid dispersal system of claim 1, wherein the sprayer head includes a housing, the housing including a light fairing protecting the ultraviolet lighting element.

4. The fluid dispersal system of claim 1, wherein the surface area illuminated by the ultraviolet light is sprayed by the fluid via the spray nozzle.

5. The fluid dispersal system of claim 4, wherein the ultraviolet lighting element directs ultraviolet light on a surface having material containing a chemical not visible to the naked human eye.

6. The fluid dispersal system of claim 1, wherein the nozzle is an adjustable nozzle that may be controlled to adjust the manner in which the fluid is dispersed.

7. The fluid dispersal system of claim 1, wherein the adjustable nozzle may be controlled to adjust the type of spray stream.

8. The fluid dispersal system of claim 1, wherein the adjustable nozzle may controlled to adjust the volume of spray.

9. The fluid dispersal system of claim 1, wherein the adjustable nozzle is a rotary nozzle with a plurality of different settings, wherein the rotary nozzle may be rotated from one setting to another in order to adjust the manner in which the fluid is dispersed.

10. The fluid dispersal system of claim 1, wherein one or more portions of the sprayer head utilize glow-in-the-dark material to aid in illuminating mode status of the adjustable nozzle in the dark.

11. The fluid dispersal system of claim 2, wherein the sprayer head includes a housing comprised of left and right "clamshell"-style housing portions that fit symmetrically, around elements of the pump system, about an axis defined by the spray direction.

12. The fluid dispersal system of claim 3, wherein the light fairing utilizes glow-in-the-dark material to aid user experience in the dark.

13. A fluid dispersal system with integrated lighting, comprising:
    a reservoir of non-pressurized cleaning and sanitizing fluid;
    a sprayer head connected to the fluid reservoir;
    a nozzle, disposed on and/or in the sprayer head and in fluid communication with the reservoir, to disperse fluid from the reservoir in a spray direction;
    a pump system that supplies the fluid from the reservoir to the nozzle;
    a lighting element, disposed on and/or in the sprayer head adjacent the spray nozzle, that directs non-focused light in a direction generally parallel to the spray direction to illuminate an area of a surface to be cleaned;
    a moveable, finger-operated trigger that is mechanically linked to the pump system, wherein the trigger is pulled to cause the pump system to disperse fluid via the nozzle; and
    an electrical switch, carried on the moveable, finger-operated trigger, that is electrically linked to the lighting element, wherein the electrical switch is actuated by force applied in the same direction as that used to pull the trigger, and wherein actuation of the electrical switch causes activation of the lighting element;
    wherein, in a first use state, the trigger is pulled by a user, without applying force to the electrical switch on the trigger, to spray the fluid without activating lighting element, and in a second use state, the trigger is pulled by the user, by applying force to the electrical switch on the trigger, to spray the fluid and simultaneously, and with the same motion, to activate the lighting element.

* * * * *